United States Patent
McGurk et al.

(10) Patent No.: US 7,766,891 B2
(45) Date of Patent: Aug. 3, 2010

(54) LUNG DEVICE WITH SEALING FEATURES

(75) Inventors: Erin McGurk, Palo Alto, CA (US);
Ronald Dieck, Palo Alto, CA (US);
Mark Mathis, Fremont, CA (US);
Charles Wartchow, Belmont, CA (US)

(73) Assignee: PneumRx, Inc., Mountain View, CA (US)

( * ) Notice: Subject to any disclaimer, the term of this patent is extended or adjusted under 35 U.S.C. 154(b) by 1381 days.

(21) Appl. No.: 11/178,243

(22) Filed: Jul. 8, 2005

(65) Prior Publication Data
US 2006/0025815 A1    Feb. 2, 2006

Related U.S. Application Data

(60) Provisional application No. 60/586,683, filed on Jul. 8, 2004.

(51) Int. Cl.
*A61M 31/00* (2006.01)
(52) U.S. Cl. .................................... 604/506
(58) Field of Classification Search ............... 604/131, 604/164.01, 500, 506, 27, 28; 600/566, 567, 600/573, 579, 562; 606/214, 41, 45; 128/898
See application file for complete search history.

(56) References Cited

U.S. PATENT DOCUMENTS

| | | |
|---|---|---|
| 3,559,652 A | 2/1971 | Banitt et al. |
| 4,013,080 A | 3/1977 | Froning |
| 4,153,058 A | 5/1979 | Nehme |
| 4,233,984 A | 11/1980 | Walling |
| 4,479,792 A | 10/1984 | Lazarus et al. |
| 4,532,935 A | 8/1985 | Wang |
| 4,702,260 A | 10/1987 | Wang |
| 4,739,760 A | 4/1988 | Chin et al. |
| 4,766,906 A | 8/1988 | Wang |

(Continued)

FOREIGN PATENT DOCUMENTS

FR    2840796    12/2003

(Continued)

OTHER PUBLICATIONS

Hermanson, Greg T. 1996, *Bioconjugate Techniques*. San Diego: Academic Press, Inc.

(Continued)

*Primary Examiner*—Manuel A Mendez
(74) *Attorney, Agent, or Firm*—Townsend and Townsend and Crew LLP

(57) ABSTRACT

This invention relates generally to a design of lung devices for safely performing a transthoracic procedure. In particular, the invention provides devices and methods of using these devices to access the thoracic cavity with minimal risk of causing pneumothorax or hemothorax. More specifically, the invention enables diagnostic and therapeutic access to a thoracic cavity using large bore instruments. This invention also provides a method for diagnostic and therapeutic procedures using a device capable of sealing the wound upon withdrawal of the device. The invention includes a device comprising an elongated body adapted to make contact with a tissue of a subject through an access hole, and a sealant delivery element. The invention also includes a method of performing tissue treatment or diagnosis in a subject.

16 Claims, 19 Drawing Sheets

U.S. PATENT DOCUMENTS

| | | | |
|---|---|---|---|
| 4,769,017 A | 9/1988 | Fath et al. | |
| 4,880,015 A | 11/1989 | Nierman | |
| 5,056,529 A | 10/1991 | de Groot | |
| 5,084,012 A | 1/1992 | Kelman | |
| 5,108,368 A | 4/1992 | Hammerslag et al. | |
| 5,165,420 A | 11/1992 | Strickland | |
| 5,186,167 A | 2/1993 | Kolobow | |
| 5,190,546 A | 3/1993 | Jervis | |
| 5,219,895 A | 6/1993 | Kelman | |
| 5,240,011 A | 8/1993 | Assa | |
| 5,261,889 A | 11/1993 | Laine et al. | |
| 5,312,329 A | 5/1994 | Beaty et al. | |
| 5,312,331 A | 5/1994 | Knoepfler | |
| 5,315,992 A | 5/1994 | Dalton | |
| 5,334,183 A | 8/1994 | Wuchinich | |
| 5,354,287 A | 10/1994 | Wacks | |
| 5,423,830 A | 6/1995 | Schneebaum et al. | |
| 5,484,401 A | 1/1996 | Rodriguez et al. | |
| 5,514,536 A | 5/1996 | Taylor | |
| 5,526,821 A | 6/1996 | Jamshidi | |
| 5,549,904 A | 8/1996 | Juergensen et al. | |
| 5,599,294 A | 2/1997 | Edwards et al. | |
| 5,660,175 A | 8/1997 | Dayal | |
| 5,660,185 A | 8/1997 | Shmulewitz et al. | |
| 5,697,365 A | 12/1997 | Pell | |
| 5,735,264 A | 4/1998 | Siczek et al. | |
| 5,736,132 A | 4/1998 | Juergensen et al. | |
| 5,750,657 A | 5/1998 | Edwardson et al. | |
| 5,846,235 A | 12/1998 | Pasricha et al. | |
| 5,916,210 A | 6/1999 | Winston | |
| 5,916,212 A | 6/1999 | Baust et al. | |
| 5,938,635 A | 8/1999 | Kuhle | |
| 5,954,636 A | 9/1999 | Schwartz et al. | |
| 5,957,919 A | 9/1999 | Laufer | |
| 5,964,770 A | 10/1999 | Flomenblit et al. | |
| 5,972,026 A | 10/1999 | Laufer et al. | |
| 5,978,697 A | 11/1999 | Maytal et al. | |
| 6,066,090 A | 5/2000 | Yoon | |
| 6,080,113 A | 6/2000 | Heneveld et al. | |
| 6,083,255 A | 7/2000 | Laufer et al. | |
| 6,174,323 B1 | 1/2001 | Biggs et al. | |
| 6,183,498 B1 | 2/2001 | Devore et al. | |
| 6,200,333 B1 | 3/2001 | Laufer | |
| 6,258,100 B1 | 7/2001 | Alferness et al. | |
| 6,267,732 B1 | 7/2001 | Heneveld et al. | |
| 6,273,907 B1 | 8/2001 | Laufer | |
| 6,280,399 B1* | 8/2001 | Rossin et al. | 600/567 |
| 6,283,988 B1 | 9/2001 | Laufer et al. | |
| 6,283,989 B1 | 9/2001 | Laufer et al. | |
| 6,287,290 B1* | 9/2001 | Perkins et al. | 604/516 |
| 6,287,304 B1 | 9/2001 | Eggers et al. | |
| 6,293,951 B1 | 9/2001 | Alferness et al. | |
| 6,299,633 B1 | 10/2001 | Laufer | |
| 6,310,166 B1 | 10/2001 | Hickey et al. | |
| 6,312,428 B1 | 11/2001 | Eggers et al. | |
| 6,315,737 B1 | 11/2001 | Skinner | |
| 6,328,689 B1 | 12/2001 | Gonzalez et al. | |
| 6,328,701 B1 | 12/2001 | Terwilliger | |
| 6,352,503 B1 | 3/2002 | Matsui et al. | |
| 6,379,373 B1 | 4/2002 | Sawhney et al. | |
| 6,387,044 B1 | 5/2002 | Tachibana et al. | |
| 6,390,967 B1 | 5/2002 | Forman et al. | |
| 6,398,775 B1 | 6/2002 | Perkins et al. | |
| 6,402,701 B1 | 6/2002 | Kaplan et al. | |
| 6,402,754 B1 | 6/2002 | Gonzalez | |
| 6,411,852 B1 | 6/2002 | Danek et al. | |
| 6,416,554 B1 | 7/2002 | Alferness et al. | |
| 6,443,944 B1 | 9/2002 | Doshi et al. | |
| 6,447,534 B2 | 9/2002 | Cragg et al. | |
| 6,464,648 B1 | 10/2002 | Nakamura | |
| 6,478,730 B1 | 11/2002 | Bala et al. | |
| 6,485,407 B2 | 11/2002 | Alferness et al. | |
| 6,485,436 B1 | 11/2002 | Truckai et al. | |
| 6,488,673 B1 | 12/2002 | Laufer et al. | |
| 6,491,706 B1 | 12/2002 | Alferness et al. | |
| 6,494,844 B1 | 12/2002 | Van Bladel et al. | |
| 6,494,897 B2 | 12/2002 | Sterman et al. | |
| 6,509,031 B1 | 1/2003 | Miller et al. | |
| 6,514,290 B1 | 2/2003 | Loomas | |
| 6,514,522 B2 | 2/2003 | Domb | |
| 6,527,761 B1 | 3/2003 | Soltesz et al. | |
| 6,537,195 B2 | 3/2003 | Forman | |
| 6,537,314 B2 | 3/2003 | Langberg et al. | |
| 6,540,694 B1 | 4/2003 | Van Bladel et al. | |
| 6,540,716 B1 | 4/2003 | Holm | |
| 6,549,800 B1 | 4/2003 | Atalar et al. | |
| 6,551,255 B2 | 4/2003 | Van Bladel et al. | |
| 6,551,302 B1 | 4/2003 | Rosinko et al. | |
| 6,552,172 B2 | 4/2003 | Marx et al. | |
| 6,558,337 B2 | 5/2003 | Dvorak et al. | |
| 6,568,387 B2 | 5/2003 | Davenport et al. | |
| 6,569,166 B2 | 5/2003 | Gonzalez | |
| 6,577,893 B1 | 6/2003 | Besson et al. | |
| 6,585,639 B1 | 7/2003 | Kotmel et al. | |
| 6,589,161 B2 | 7/2003 | Corcoran | |
| 6,592,559 B1 | 7/2003 | Pakter et al. | |
| 6,592,594 B2 | 7/2003 | Rimbaugh et al. | |
| 6,599,311 B1 | 7/2003 | Biggs et al. | |
| 6,610,043 B1 | 8/2003 | Ingenito | |
| 6,622,731 B2 | 9/2003 | Daniel et al. | |
| 6,629,951 B2 | 10/2003 | Laufer et al. | |
| 6,632,222 B1 | 10/2003 | Edwards et al. | |
| 6,632,239 B2 | 10/2003 | Snyder et al. | |
| 6,632,243 B1 | 10/2003 | Zadno-Azizi et al. | |
| 6,634,363 B1 | 10/2003 | Danek et al. | |
| 6,638,275 B1 | 10/2003 | McGaffigan et al. | |
| 6,652,516 B1 | 11/2003 | Gough | |
| 6,652,520 B2 | 11/2003 | Moorman et al. | |
| 6,653,525 B2 | 11/2003 | Ingenito et al. | |
| 6,663,624 B2 | 12/2003 | Edwards et al. | |
| 6,679,264 B1 | 1/2004 | Deem et al. | |
| 6,682,520 B2 | 1/2004 | Ingenito | |
| 6,685,626 B2 | 2/2004 | Wironen | |
| 6,689,072 B2 | 2/2004 | Kaplan et al. | |
| 6,690,976 B2 | 2/2004 | Fenn et al. | |
| 6,692,494 B1 | 2/2004 | Cooper et al. | |
| 6,694,979 B2 | 2/2004 | Deem et al. | |
| 6,695,791 B2 | 2/2004 | Gonzalez | |
| 6,709,401 B2 | 3/2004 | Perkins et al. | |
| 6,709,408 B2 | 3/2004 | Fisher | |
| 6,709,456 B2 | 3/2004 | Langberg et al. | |
| 6,712,812 B2 | 3/2004 | Roschak et al. | |
| 6,716,180 B2 | 4/2004 | Fontenot | |
| 6,723,095 B2 | 4/2004 | Hammerslag | |
| 6,730,044 B2 | 5/2004 | Stephens et al. | |
| 6,736,822 B2 | 5/2004 | McClellan et al. | |
| 6,749,606 B2 | 6/2004 | Keast et al. | |
| 6,752,767 B2 | 6/2004 | Turovskiy et al. | |
| 6,752,812 B1 | 6/2004 | Truwit | |
| 6,758,824 B1 | 7/2004 | Miller et al. | |
| 6,768,425 B2 | 7/2004 | Flaherty et al. | |
| 6,770,066 B1 | 8/2004 | Weaver et al. | |
| 6,770,070 B1* | 8/2004 | Balbierz | 606/41 |
| 6,789,545 B2 | 9/2004 | Littrup et al. | |
| 6,790,172 B2 | 9/2004 | Alferness et al. | |
| 6,790,185 B1 | 9/2004 | Fisher et al. | |
| 6,797,001 B2 | 9/2004 | Mathis et al. | |
| 6,807,446 B2 | 10/2004 | Fenn et al. | |
| 6,808,525 B2 | 10/2004 | Latterell et al. | |
| 6,817,973 B2 | 11/2004 | Merril et al. | |
| 6,825,091 B2 | 11/2004 | Bae et al. | |
| 6,827,086 B2 | 12/2004 | Shuman | |
| 6,830,756 B2 | 12/2004 | Hnojewyj | |
| 6,840,243 B2 | 1/2005 | Deem et al. | |

| | | |
|---|---|---|
| 6,840,948 B2 | 1/2005 | Albrecht et al. |
| 6,840,952 B2 | 1/2005 | Saker et al. |
| 6,843,767 B2 | 1/2005 | Corcoran et al. |
| 6,849,262 B2 | 2/2005 | Ollerenshaw et al. |
| 6,852,108 B2 | 2/2005 | Barry et al. |
| 6,860,847 B2 | 3/2005 | Alferness et al. |
| 6,863,676 B2 | 3/2005 | Lee et al. |
| 6,875,209 B2 | 4/2005 | Zvuloni et al. |
| 6,878,106 B1 | 4/2005 | Herrmann |
| 6,878,141 B1 | 4/2005 | Perkins et al. |
| 6,886,558 B2 | 5/2005 | Tanaka |
| 6,901,927 B2 | 6/2005 | Deem et al. |
| 6,902,526 B2 | 6/2005 | Katzman |
| 6,902,536 B2 | 6/2005 | Manna et al. |
| 6,904,909 B2 | 6/2005 | Andreas et al. |
| 6,908,440 B2 | 6/2005 | Fisher |
| 6,918,881 B2 | 7/2005 | Miller et al. |
| 6,936,014 B2 | 8/2005 | Vetter et al. |
| 6,942,627 B2 | 9/2005 | Huitema |
| 6,945,942 B2 | 9/2005 | Van Bladel et al. |
| 6,962,587 B2 | 11/2005 | Johnson et al. |
| 6,964,662 B2 | 11/2005 | Kidooka |
| 6,967,673 B2 | 11/2005 | Ozawa et al. |
| 2002/0007831 A1 | 1/2002 | Davenport et al. |
| 2002/0026188 A1 | 2/2002 | Balbierz et al. |
| 2002/0042564 A1 | 4/2002 | Cooper et al. |
| 2002/0042565 A1 | 4/2002 | Cooper et al. |
| 2002/0062120 A1 | 5/2002 | Perkins et al. |
| 2002/0077593 A1 | 6/2002 | Perkins et al. |
| 2002/0091379 A1 | 7/2002 | Danek et al. |
| 2002/0111620 A1 | 8/2002 | Cooper et al. |
| 2002/0112729 A1 | 8/2002 | DeVore et al. |
| 2002/0128647 A1 | 9/2002 | Roschak et al. |
| 2002/0138074 A1 | 9/2002 | Keast et al. |
| 2002/0161399 A1 | 10/2002 | Cruise et al. |
| 2002/0176893 A1 | 11/2002 | Wironen et al. |
| 2002/0183244 A1 | 12/2002 | Ollerenshaw et al. |
| 2002/0183838 A1 | 12/2002 | Liddicoat et al. |
| 2002/0188171 A1 | 12/2002 | Alferness et al. |
| 2003/0018318 A1 | 1/2003 | Melsky |
| 2003/0029452 A1 | 2/2003 | Suki et al. |
| 2003/0050648 A1 | 3/2003 | Alferness et al. |
| 2003/0051733 A1 | 3/2003 | Kotmel et al. |
| 2003/0055331 A1 | 3/2003 | Kotmel et al. |
| 2003/0069488 A1 | 4/2003 | Alferness et al. |
| 2003/0070676 A1 | 4/2003 | Cooper et al. |
| 2003/0070683 A1 | 4/2003 | Deem et al. |
| 2003/0075170 A1 | 4/2003 | Deem et al. |
| 2003/0083671 A1 | 5/2003 | Rimbaugh et al. |
| 2003/0100921 A1 | 5/2003 | Addis et al. |
| 2003/0109866 A1 | 6/2003 | Edwards et al. |
| 2003/0127090 A1 | 7/2003 | Gifford et al. |
| 2003/0130657 A1 | 7/2003 | Tom et al. |
| 2003/0154988 A1 | 8/2003 | DeVore et al. |
| 2003/0158515 A1 | 8/2003 | Gonzalez et al. |
| 2003/0159700 A1 | 8/2003 | Laufer et al. |
| 2003/0181356 A1 | 9/2003 | Ingenito |
| 2003/0181922 A1 | 9/2003 | Alferness |
| 2003/0183235 A1 | 10/2003 | Rimbaugh et al. |
| 2003/0191496 A1 | 10/2003 | Edwards et al. |
| 2003/0195385 A1 | 10/2003 | DeVore |
| 2003/0195511 A1 | 10/2003 | Barry |
| 2003/0212337 A1 | 11/2003 | Sirokman |
| 2003/0212412 A1 | 11/2003 | Dillard et al. |
| 2003/0233099 A1 | 12/2003 | Danaek et al. |
| 2004/0010209 A1 | 1/2004 | Sirokman |
| 2004/0010289 A1 | 1/2004 | Biggs et al. |
| 2004/0024356 A1 | 2/2004 | Tanaka |
| 2004/0030262 A1 | 2/2004 | Fisher et al. |
| 2004/0031494 A1 | 2/2004 | Danek et al. |
| 2004/0038868 A1 | 2/2004 | Ingenito |
| 2004/0040555 A1 | 3/2004 | Tanaka |
| 2004/0049187 A1 | 3/2004 | Burnett et al. |
| 2004/0052850 A1 | 3/2004 | Schankereli |
| 2004/0055606 A1 | 3/2004 | Hendricksen et al. |
| 2004/0059263 A1 | 3/2004 | DeVore et al. |
| 2004/0063613 A1 | 4/2004 | Rolke et al. |
| 2004/0072756 A1 | 4/2004 | Wilkie et al. |
| 2004/0073155 A1 | 4/2004 | Laufer et al. |
| 2004/0073191 A1 | 4/2004 | Soltesz et al. |
| 2004/0073201 A1 | 4/2004 | Cooper et al. |
| 2004/0073241 A1 | 4/2004 | Barry et al. |
| 2004/0078054 A1 | 4/2004 | Biggs et al. |
| 2004/0081676 A1 | 4/2004 | Schankereli et al. |
| 2004/0120849 A1 | 6/2004 | Stewart et al. |
| 2004/0133168 A1 | 7/2004 | Salcudean et al. |
| 2004/0158228 A1 | 8/2004 | Perkins |
| 2004/0172058 A1 | 9/2004 | Edwards et al. |
| 2004/0176801 A1 | 9/2004 | Edwards et al. |
| 2004/0210248 A1 | 10/2004 | Gordon et al. |
| 2004/0211434 A1 | 10/2004 | Loomas et al. |
| 2004/0220556 A1 | 11/2004 | Cooper et al. |
| 2004/0225254 A1 | 11/2004 | Tanaka et al. |
| 2004/0231674 A1 | 11/2004 | Tanaka |
| 2004/0234575 A1 | 11/2004 | Horres et al. |
| 2004/0237966 A1 | 12/2004 | Tanaka |
| 2004/0244802 A1 | 12/2004 | Tanaka |
| 2004/0244803 A1 | 12/2004 | Tanaka |
| 2005/0004599 A1 | 1/2005 | McNally-Heintzelman et al. |
| 2005/0015106 A1 | 1/2005 | Perkins et al. |
| 2005/0043751 A1 | 2/2005 | Phan et al. |
| 2005/0043752 A1 | 2/2005 | Phan et al. |
| 2005/0049615 A1 | 3/2005 | Cooper et al. |
| 2005/0060041 A1 | 3/2005 | Phan et al. |
| 2005/0060042 A1 | 3/2005 | Phan et al. |
| 2005/0061322 A1 | 3/2005 | Freitag |
| 2005/0085801 A1 | 4/2005 | Cooper et al. |
| 2005/0096529 A1 | 5/2005 | Cooper et al. |
| 2005/0107783 A1 | 5/2005 | Tom et al. |
| 2005/0119614 A1 | 6/2005 | Melsky |
| 2005/0281739 A1 | 12/2005 | Gong et al. |
| 2005/0281740 A1 | 12/2005 | Gong et al. |
| 2005/0281796 A1 | 12/2005 | Gong et al. |
| 2005/0281797 A1 | 12/2005 | Gong et al. |
| 2005/0281798 A1 | 12/2005 | Gong et al. |
| 2005/0281799 A1 | 12/2005 | Gong et al. |
| 2005/0281800 A1 | 12/2005 | Gong et al. |
| 2005/0281801 A1 | 12/2005 | Gong et al. |
| 2005/0281802 A1 | 12/2005 | Gong et al. |
| 2005/0282748 A1 | 12/2005 | Gong et al. |
| 2005/0288549 A1 | 12/2005 | Mathis |
| 2005/0288550 A1 | 12/2005 | Mathis |
| 2005/0288684 A1 | 12/2005 | Aronson et al. |
| 2005/0288702 A1 | 12/2005 | McGurk et al. |
| 2006/0004400 A1 | 1/2006 | McGurk et al. |
| 2006/0009748 A1 | 1/2006 | Mathis |
| 2006/0009801 A1 | 1/2006 | McGurk et al. |
| 2006/0167416 A1 | 7/2006 | Mathis et al. |
| 2007/0221230 A1 | 9/2007 | Thompson et al. |

FOREIGN PATENT DOCUMENTS

| | | |
|---|---|---|
| GB | 2324729 B | 1/2002 |
| WO | WO 00/13592 A1 | 3/2000 |
| WO | WO 01/13839 A1 | 3/2001 |
| WO | WO 01/70114 A1 | 9/2001 |
| WO | WO 02/00270 A1 | 1/2002 |
| WO | WO 02/00275 A1 | 1/2002 |
| WO | WO 02/02158 A1 | 1/2002 |
| WO | WO 03/077768 A1 | 9/2003 |
| WO | WO 2004/012678 A2 | 2/2004 |
| WO | WO 2004/062505 A1 | 7/2004 |
| WO | WO 2004/086977 A1 | 10/2004 |
| WO | WO 2006/014567 A2 | 2/2006 |
| WO | WO 2006/058195 A2 | 6/2006 |

WO WO 2006/058195 A3 6/2006

OTHER PUBLICATIONS

Lam, K.N. Sin Fai et al. 1998. X-Ray Diagnosis: A Physician's Approach. Singapore: Springer.
Rowe, Raymond C., et al. 2003. *Handbook of Pharmaceutical Excipients* 4th Edition . London: Pharmaceutical Press.
Slone, Richard M. et al. 2000. Body CT: A Practical Approach. New York: McGraw-Hill.
Stout, George H. et al. 1989. X-Ray Structure Determination: A Practical Guide, 2nd Edition. New York: John Wiley & Sons.
The United States Pharmacopeia, 29th Revision. 2006. The United States Pharmacopeial Convention.
Mathis, M., U.S. Appl. No. 11/286,445 entitled "Steerable Device for Accessing a Target Site and Methods", filed Nov. 23, 2005.
Extended European Search Report of EP Application No. 05792375.7, mailed Aug. 27, 2009, 10 pages total.

* cited by examiner

LUNG DEVICE WITH SEALING FEATURES

CROSS-REFERENCE

This application claims the benefit of U.S. Provisional Application No. 60/586,683, filed Jul. 8, 2004, which is incorporated herein by reference in its entirety.

BACKGROUND OF THE INVENTION

1. Field of the Invention

This invention relates generally to a design of lung devices for safely performing a transthoracic procedure. In particular, the invention provides devices and methods of using these devices to access the thoracic cavity with minimal risk of causing pneumothorax or hemothorax. More specifically, the invention enables diagnostic and therapeutic access to a thoracic cavity using large bore instruments. This invention also provides a method for diagnostic and therapeutic procedures using a device capable of sealing the wound upon withdrawal of the device.

2. Description of Related Art

Pulmonary disorders affect millions of Americans, and many more individuals worldwide, each year. While some pulmonary disorders are chronic (e.g., chronic obstructive pulmonary disease (COPD)), many are acute and deadly. For example, lung cancer is the leading cause of death attributable to cancer for both men and women. More people die of lung cancer, than die of breast, prostate and colon cancer combined. It is estimated that in the United States alone, over 170,000 new cases of lung cancer are diagnosed each year. Of those people diagnosed with lung cancer, the prognosis is grim: 6 of 10 will die within one year of being diagnosed and between 7 and 8 will die within two years of diagnosis.

Most lung cancers start in the lining of the bronchi (plural for bronchus), although lung cancer can start in other parts of the lung as well. Since it generally takes many years for lung cancer to develop, there can be areas of pre-cancerous changes in the lung long before the formation of lung cancer. With currently available technology, the pre-cancerous changes are often not detected because the changes cannot be seen on an x-ray and do not cause symptoms early on that would cause a patient to seek medical attention. It is for this reason that most people with lung cancer are not diagnosed during the critical early stages of the disease.

Taking chest x-rays and checking sputum under a microscope for the appearance of cancer cells had been performed for screening but was found to be unreliable, and thus is not even recommended screening for persons of high risk (e.g., those people who smoke). Recently, spiral CT scanning has shown promise as a potential screening tool for finding lung cancer at an early stage. However, at this juncture it is not known whether the use of spiral CT scans improve the prognosis for long-term survival by increasing the early detection of the disease. Even with a scan indicating the possible presence of pre-cancerous tissue, the ability to take a biopsy for testing is difficult without causing the lungs to collapse, which can result in a required hospital stay.

Thus, with the current state of the art, any time a procedure requires an instrument to be inserted through an incision in the chest wall, the pleural layers surrounding the lung are pierced or compromised. As a result of the propensity for transthoracic procedures to cause, for example, pneumothorax, there is a limitation on the outer diameter of the instruments that are used for these procedures. This is a significant drawback for procedures such as percutnaeous transthoracic lung tissue biopsy, where the interventionalist introduces a biopsy needle through the chest wall. Other procedures which are limited when applied to transthoracic procedures include percutaneous transthoracic needle aspiration (PTNA), mediastinoscopy, thorascopy and drainage of pleural effusions. Air leaks and bleeding frequently occur either during insertion or removal of the device through the opening in the pleural lining of the chest cavity. Even when using small needles of 19-23 gauge, the incidence of pneumothorax is relatively high, being in the range of 30-40% and the incidence of hemothorax is 25%. For this reason, larger bore instruments (e.g., having a gauge of less than 19 and therefore a larger diameter) are not typically used to access the lung through the chest cavity, and practitioners are substantially limited in the amount of tissue accessible or treatable using a percutaneous procedure. More importantly, practitioners do not fully benefit from minimally invasive techniques commonly used for diagnostic and therapeutic procedures that are easily performed in other areas of the body (e.g., the breast), when treating the lung.

Treatment options for pneumothorax or hemothorax include intubation, wherein a tube is inserted through the chest wall into the pleural space to withdraw the air or fluid. In that instance, the tube is typically left in place and attached to a drainage system for several days, which requires the patient to be hospitalized. In some circumstances, such as where bleeding occurs, surgical intervention may be required.

Even during the biopsy process currently practiced, multiple samples or cores of tissue are taken through the smallest gauge needle possible in an effort to increase biopsy efficacy while decreasing the likelihood of, for example, pneumothorax. However, each time the needle is reinserted, the chances for pneumothorax or bleeding increase. Additionally, due to the small size of the multiple samples, the pathologist does not have the benefit of a larger sample size that would improve the accuracy of diagnosis.

Thus, there exists a considerable need for devices and methods that provide minimally invasive access to the lung for diagnostics and treatment but which do not risk causing the lung to collapse, or air or blood entering the pleural space. Additionally, what is needed is a tool that enables potentially cancerous tissue to be removed (e.g., for a biopsy) but which prevents cells from migrating along the tract used by the tool to access the tissue. The present invention satisfies these need and provides related advantages as well.

SUMMARY OF THE INVENTION

The present invention provides devices and methods for performing a diagnostic or therapeutic transthoracic procedure with minimal risk of a complications, such as a pneumothorax or hemothorax. The present invention also includes pre-treating and/or sealing a site of therapeutic or diagnostic intervention. Compositions are used in combination with the methods and devices disclosed. Other methods and compositions are also provided in U.S. patent applications entitled "Pleural Effusion Treatment Device, Method and Material" application Ser. No. 11/177,926 filed Jul. 8, 2005; "Intra-Bronchial Lung Volume Reduction System," application Ser. No. 11/153,235 filed Jun. 14, 2005; "Targeting Damaged Lung Tissue Using Compositions," application Ser. No. 11/008,577, filed Dec. 8, 2004; "Targeting Damaged Lung Tissue," application Ser. No. 11/008,092, filed Dec. 8, 2004; "Targeting Sites of Damaged Lung Tissue Using Composition," application Ser. No. 11/008,094 filed Dec. 8, 2004; "Targeting Sites of Damaged Lung Tissue," application Ser. No. 11/008,578, filed Dec. 8, 2004; "Imaging Damaged Lung Tissue Using Compositions," application Ser. No. 11/008,649, filed Dec. 8, 2004; "Imaging Damaged Lung Tissue," application Ser. No. 11/008,777, filed Dec. 8, 2004; "Lung Volume Reduction Using Glue Compositions," application Ser. No. 11/008,093, filed Dec. 8, 2004; "Glue Composition for Lung Volume Reduction," application Ser. No. 11/008,580 filed Dec. 8, 2004, "Glue Composition for Lung Volume Reduction," application Ser. No. 11/008,087 filed Dec. 8, 2004; and "Lung Volume Reduction Using Glue Composition," application Ser. No. 11/008,782 filed Dec. 8, 2004.

An embodiment of the invention disclosed herein includes a system comprising an elongated body adapted to provide access to target tissue of a subject through an access hole, a cross-linked tissue sealant, and a sealant delivery element adapted to deliver the cross-linked tissue sealant through the access hole. In some embodiments of the system, it is adapted to deliver therapy or diagnostics to the subject. Further, the sealant delivery element can be adapted to deliver sealant to the target tissue prior to performing a therapy on the target tissue, at one or more locations. Further, the sealant delivery element can be adapted to deliver a sealant to the access hole upon removal of the system and/or adapted to deliver a sealant to target tissue prior to performing diagnostics on the target tissue. More than one sealant delivery element can be provided where more than one sealant (i.e., having more than one viscosity) is desired. The distal end of the elongated body of the system can be configured on its distal end to comprise a cutting element, an imaging element, or a pharmaceutical delivery element. The system can also be disposed within an elongated sleeve. A variety of sealants are suitable for use with the system, including sealants that accelerate the clotting cascade. In some embodiments, sealant can comprise materials selected from the group consisting of hydrogels, proteins, polymers and cross-linking agents. The sealants of the invention can have an adhesion force up to 3.0. In other embodiments, it may be desirable to include a detectable label, an enzyme, a radioactive isotope, or a luminescent substance in the sealant. Typically, the sealant will have a viscosity greater than 1.1 centipose.

In another embodiment of the invention, a lung device system is provided comprising an elongated body adapted to make contact with an inner part of the lung or surrounding tissue of the lung through an access hole, a glutaraldehyde based sealant, and a hole closing element for closing the access hole adapted to deliver the glutaraldehyde based sealant through the access hole. The glutaraldehyde based sealant can be heat-treated. Further, the hole closing element can be adapted to mitigate air leakage into a space between the lung and pleural membrane. Mitigating leakage in the embodiments of the device mitigates pneumothorax and hemothorax. The device can, in some embodiments, be adapted for excising tissue, imaging tissue, and delivering pharmaceutical compositions. The sealants used in the embodiments of the invention can initiate or accelerate the clotting cascade. In some embodiments of the invention, the elongated body has a distal end and a proximal end, with the distal end comprising a cutting element. Further, a sleeve can be disposed about the elongated body. Sealants used in the embodiments of the invention are typically glutaraldehyde based sealants that are a tissue-bonding material. The glutaraldehyde based sealants suitable for the embodiments of the invention can comprise hydrogel, protein, polymer, and cross-linking agents. The adhesive force of the sealant is from 0.2 psi to 3.0 psi. It may be desirable to include a detectable label in some embodiments of the sealant. Typically, the sealant has a viscosity greater than 1.1 centipoise.

Embodiments of the invention also include a method of performing tissue treatment or diagnosis in a subject, comprising: delivering a device through an incision to a target site within the subject, the device comprising a sealant delivery element adapted to deliver a cross-linked sealant; performing treatment or diagnosis at the site; and delivering the cross-linked tissue sealant to the incision. In some embodiments, the method includes the step of delivering a cross-linked tissue sealant through the incision prior to delivering the device through the incision to the target site. Further, the target site can be a subject's lung. During the process of removing the device, cross-linked tissue sealant can be applied prior to beginning withdrawal, during withdrawal, or following withdrawal. It is anticipated that for some embodiments the sealant delivery element will be adapted to mitigate air leakage into a space between the lung and pleural membrane, including pneumothorax and hemothorax. Some embodiments of the method can employ a device that comprises an imaging element, an element adapted to deliver a pharmaceutical compound, or a cutting element. Additionally, embodiments of the method can use a device with a sealant delivery element that is a syringe or a plunger. The sealants used can be biologically compatible cross-linked tissue sealant that are tissue-bonding material. Typically the biological compatible cross-linked sealant can include hydrogels, collagen, polysalactic acid, cyano acrylates, and glutaraldehyde.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 8B illustrates the removal of the device which is sealing its entry tract during removal.

FIG. 12B illustrates the mixing chamber and delivery trocar of the device.

DETAILED DESCRIPTION OF THE INVENTION

Figure 1A:
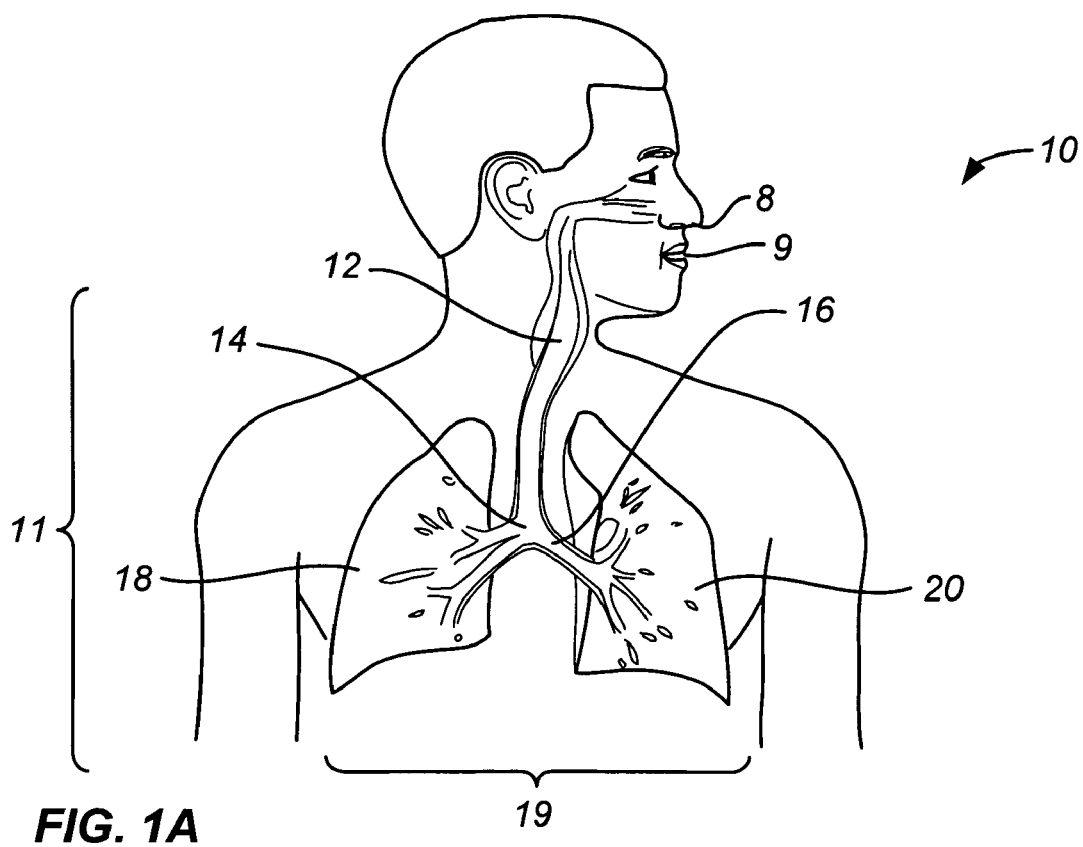
FIGS. 1A-D illustrates the anatomy of the respiratory system, along with an example of hemothorax caused from blood entering the pleural space.

As noted above, a principal aspect of the present invention is the design of lung devices that can safely perform a transthoracic procedure without impacting the negative pressure required to maintain lung function. In particular, the present devices allow accessing the interior of the lung or the surrounding tissue to perform therapeutic or diagnostic functions while reducing the risk of complications associated with the accessing procedure. The devices and methods are used with adhesive compositions that have cross-linkable moiety and adhering moiety that enable the glue to adhere to lung tissue with low toxicity. Suitable adhesives, such as glue, act as a sealant to prevent the passage of liquid or gas.

The invention provides methods, materials and devices for providing diagnostic and therapeutic treatment to a target tissue, such as lung, using a suitable adhesive, such as glue, as a sealant to prevent the passage of liquid or gas. The materials used in the method include a fast-acting adhesive that cures in less than three days, more preferably less than two days, even more preferably less than one day, and most preferably less than one hour. A specific cure time may be tunable to allow for glue distribution within the target site before curing fully. Some glue formulations may require ancillary light sources, primers, catalysts, radiofrequency energy, electrical energy or radiation to cause the glue to cure.

Glue formulations for use with this invention may include solids, semi-solids, hydrogels, foams, agars or sol-gels. Some glue formulations work in wet or dry tissue surface conditions. Some glue formulations may also stop active bleeding (i.e., provide hemostasis). The glues are preferably biocompatible and can successfully fuse tissue in wet conditions. The glues are flexible and conformable to tissue geometry, and they possess high tensile strength. Solvents can be used to deliver the glue in order to drive the glue into the tissue.

One preferred embodiment is a glue formulation that crosslinks (chemically bonds) to the biological tissue it is applied to. More specifically, the adhesive either crosslinks to collagen or promotes the crosslinking of collagen at two adjoining tissue surfaces to be fused and allow for high adhesion.

Another preferred embodiment is a glue formulation that has a radiopaque component so that the glued boundary can be identified using x-ray-based imaging techniques during or after the procedure. Additives may include tantalum, platinum, bismuth, radiopaque metals and polymers. Polymers can include, for example, poly(lactic acid) and poly(glycolide). Agents and drugs can also be added as primers.

Although many alternative glue formulations may be suitable to achieve these goals, one preferred glue formulation consists of a combination of a cross-linking agent, such as glutaraldehyde or stable polyaldehyde and a protein, such as albumin, porcine albumin and collagen, with or without additional additives. One such material suitable for use as a sealant during therapeutic and diagnostic procedures is described in US Patent Application Publ. No. 2004/0081676. The glue's intrinsic viscosity can be tuned to allow for fast or slow spreading across target regions. The glue may be used for other purposes as well, such as anastomosis of blood vessels. Another adhesive that may be suitable is a cyanoacrylate adhesive.

Alternative glue formulations may be suitable to achieve these goals such as a combination of any one of the previously described components in combination with other additives that may include elastin, fibrin, glycoprotein, liposomes, thrombin, calcium, neuroleptics, vitamins, growth factors, glucocorticosteroids, steroids, antibiotics, antibacterial compounds, bacteriocidal and bacteriostatic compounds, antiviral compounds, antifungal compounds, antiparasitic compounds, tumoricidal compounds, tumoristatic compounds, toxins, enzymes, enzyme inhibitors, proteins, peptides, minerals, neurotransmitters, lipoproteins, glycoproteins, immunomodulators, immunoglobulins and fragments thereof, dyes, radiolabels, radiopaque compounds, fluorescent compounds, fatty acids, polysaccharides, cell receptor binding molecules, anti-inflammatories, antiglaucomic compounds, mydriatic compounds, anesthetics, nucleic acids, and polynucleotides.

The glue can be packaged sterile, in a single part or in two liquid parts in an applicator. Upon delivery of a two-part formulation, liquid components can be mixed as they are delivered, by an applicator or stirring or mixing nozzle device. After application, the formulation may quickly or slowly solidify into a flexible solid glue. The glue can also be premixed and then applied. The glue may be formulated as a two part solution that can be applied independently. In doing so, the first part may be applied and allowed for spread time before the second is applied.

FIG. 1A illustrates the respiratory system 10 located primarily within a thoracic cavity 11. The respiratory system 10 includes the trachea 12, which brings air from the nose 8 or mouth 9 into the right primary bronchus 14 and the left primary bronchus 16. From the right primary bronchus 14 the air enters the right lung 18; from the left primary bronchus 16 the air enters the left lung 20. The right lung 18 and the left lung 19, together comprise the lungs 19. The left lung 20 is comprised of only two lobes while the right lung 18 is comprised of three lobes, in part to provide space for the heart typically located in the left side of the thoracic cavity 11, also referred to as the chest cavity.

Figure 1B:
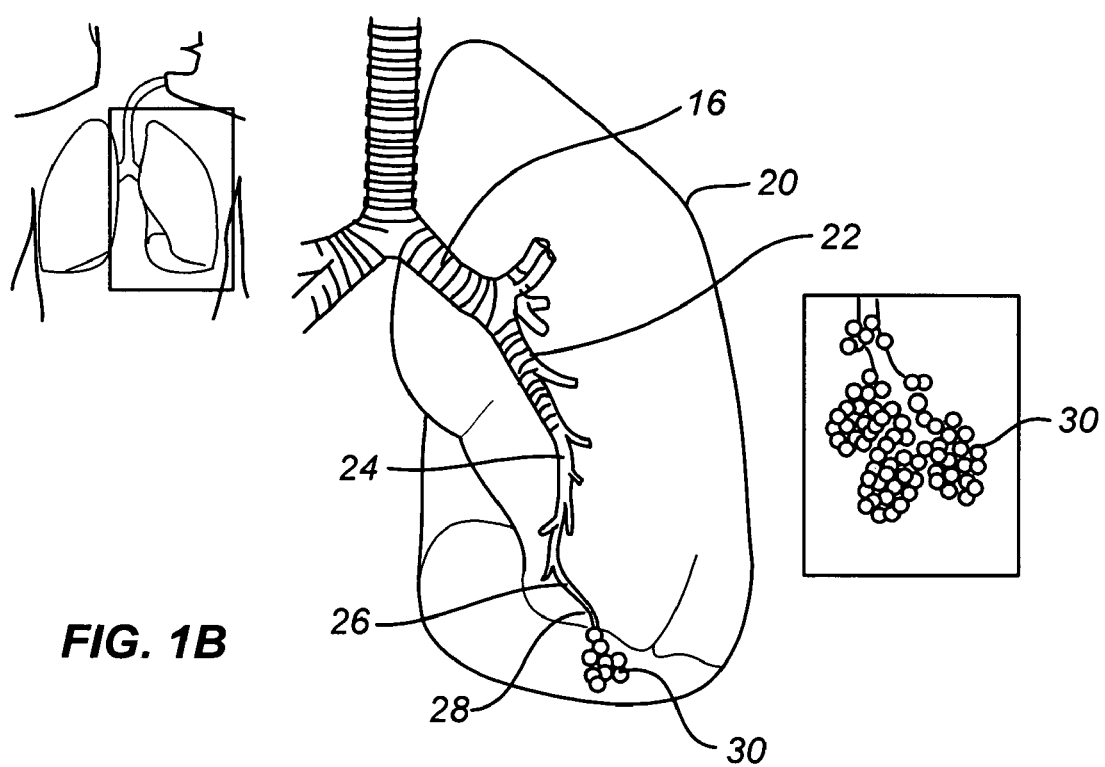
Figure 1C:
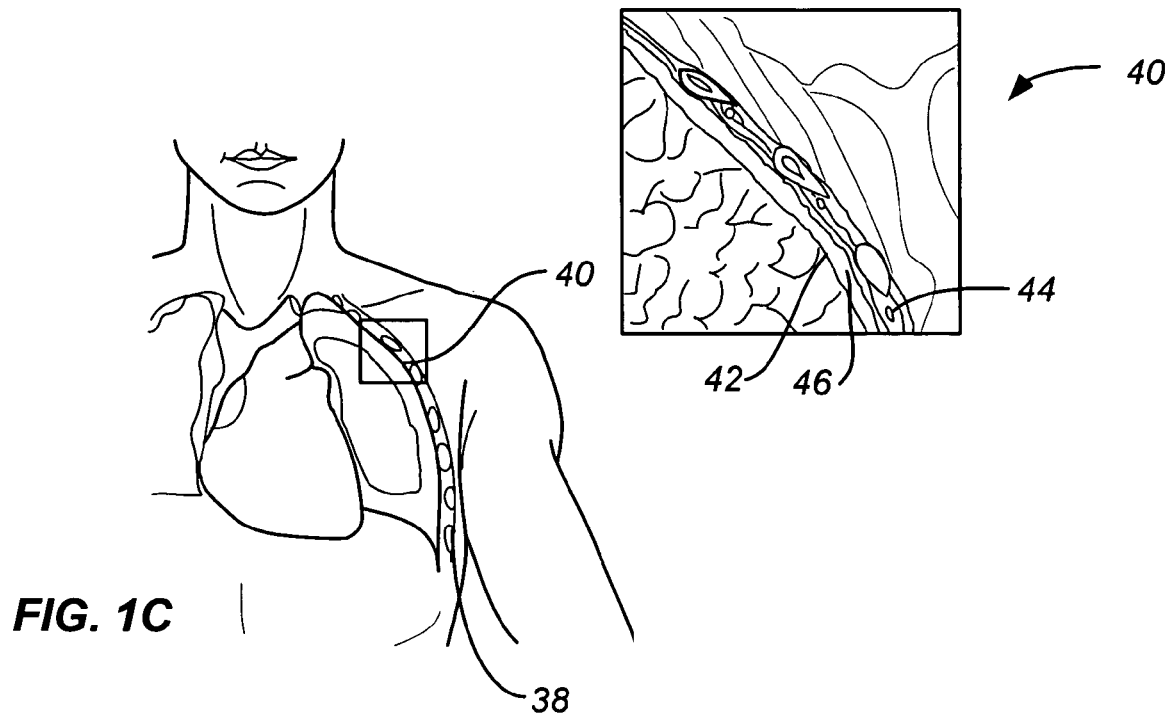

As shown in more detail in FIG. 1B, the primary bronchus, e.g. left primary bronchus 16, that leads into the lung, e.g. left lung 20, branches into secondary bronchus 22, and then further into tertiary bronchus 24, and still further into bronchioles 26, the terminal bronchiole 28 and finally the alveoli 30. The pleural cavity 38 is the space between the lungs and the chest wall. The pleural cavity 38 protects the lungs 18, 20 and allows the lungs to move during breathing. As shown in FIG. 1C, the pleura 40 defines the pleural cavity 38 and consists of two layers, the visceral pleurae 42 and the parietal pleurae 44, with a thin layer of pleural fluid therebetween. The space occupied by the pleural fluid is referred to as the pleural space 46. Each of the two pleurae layers 42, 44, are comprised of very porous mesenchymal serous membranes through which small amounts of interstitial fluid transude continually into the pleural space 46. The total amount of fluid in the pleural space 46 is typically slight. Under normal conditions, excess fluid is typically pumped out of the pleural space 46 by the lymphatic vessels.

The lungs 19 are an elastic structure that float within the thoracic cavity 11. The thin layer of pleural fluid that surrounds the lungs 19 lubricates the movement of the lungs within the thoracic cavity 11. Suction of excess fluid from the pleural space 46 into the lymphatic channels maintains a slight suction between the visceral pleural surface of the lung pleura 42 and the parietal pleural surface of the thoracic cavity 44. This slight suction creates a negative pressure that keeps the lungs 19 inflated and floating within the thoracic cavity 11. Without the negative pressure, the lungs 19 collapse like a balloon and expel air through the trachea 12. Thus, the natural process of breathing out is almost entirely passive because of the elastic recoil of the lungs 19 and chest cage structures. As a result of this physiological arrangement, when the pleura 42, 44 is breached, the negative pressure that keeps the lungs 19 in a suspended condition disappears and the lungs 19 collapse from the elastic recoil effect.

When fully expanded, the lungs 19 completely fill the pleural cavity 38 and the parietal pleurae 44 and visceral pleurae 42 come into contact. During the process of expansion and contraction with the inhaling and exhaling of air, the lungs 19 slide back and forth within the pleural cavity 38. The movement within the pleural cavity 38 is facilitated by the thin layer of mucoid fluid that lies in the pleural space 46 between the parietal pleurae 44 and visceral pleurae 42.

Figure 1D:
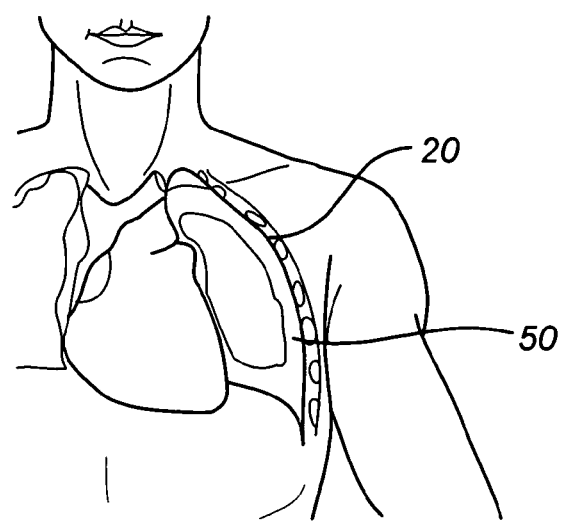

For purposes of illustration, FIG. 1D illustrates a lung 20 with blood in the pleural space 50 (also referred to as hemothorax). As evidenced from the drawing, the presence of blood 50 in the pleural space 46 results in a contraction of the lung 20 to a much smaller size. Clinically, the patient would have a difficult time breathing air into the collapsed lung because the act of breathing relies on the lungs being suspended in a state of negative pressure. As will be appreciated by those of skill in the art, fluid or air within the pleural space 46 will achieve a similar clinical impact on the size of the lung relative to the thoracic cavity as the hemothorax illustrated in FIG. 1D.

Figure 2A:
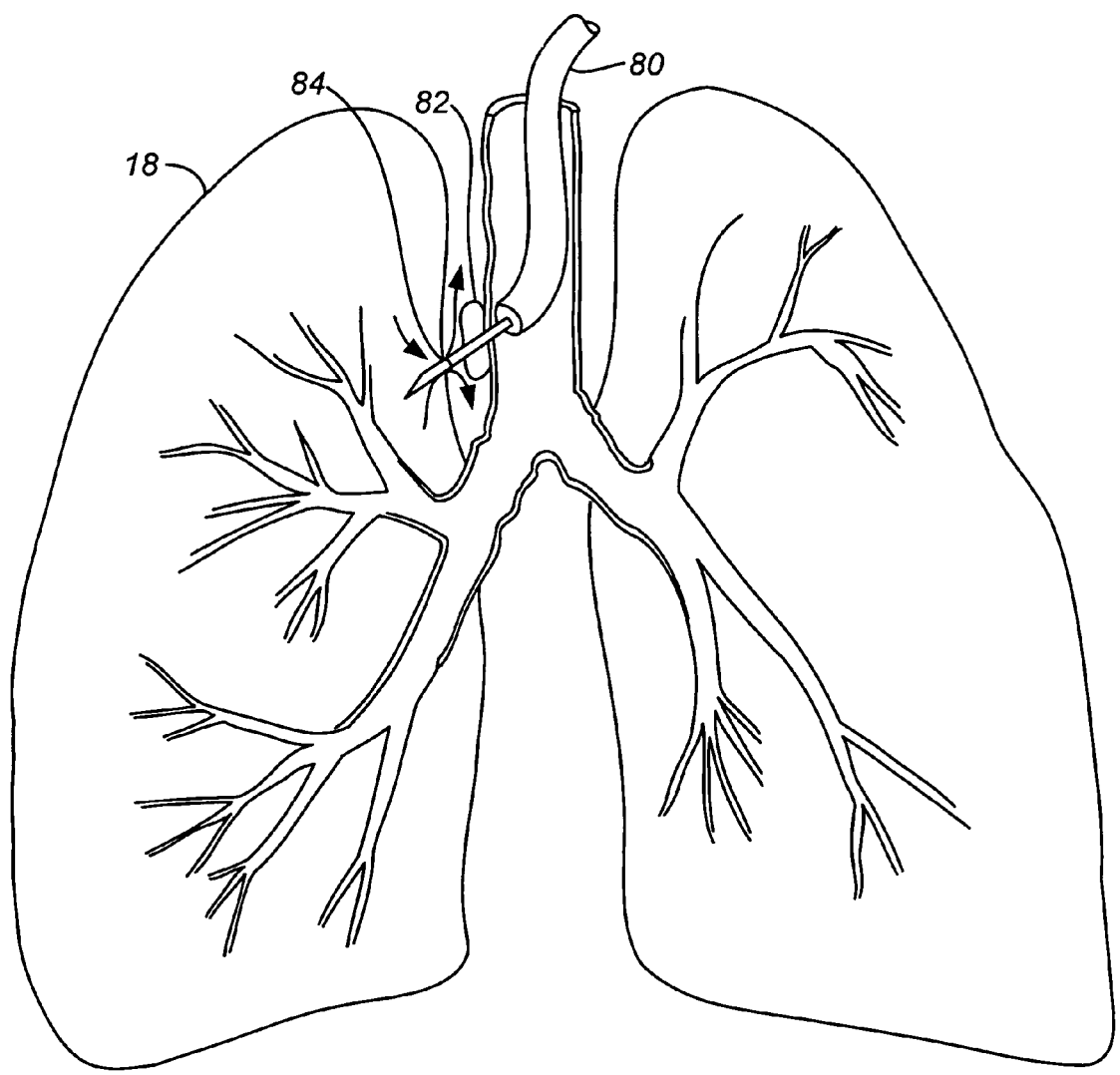
FIGS. 2A-B illustrate a lung during a procedure wherein the device breaches the pleura.
Figure 2B:
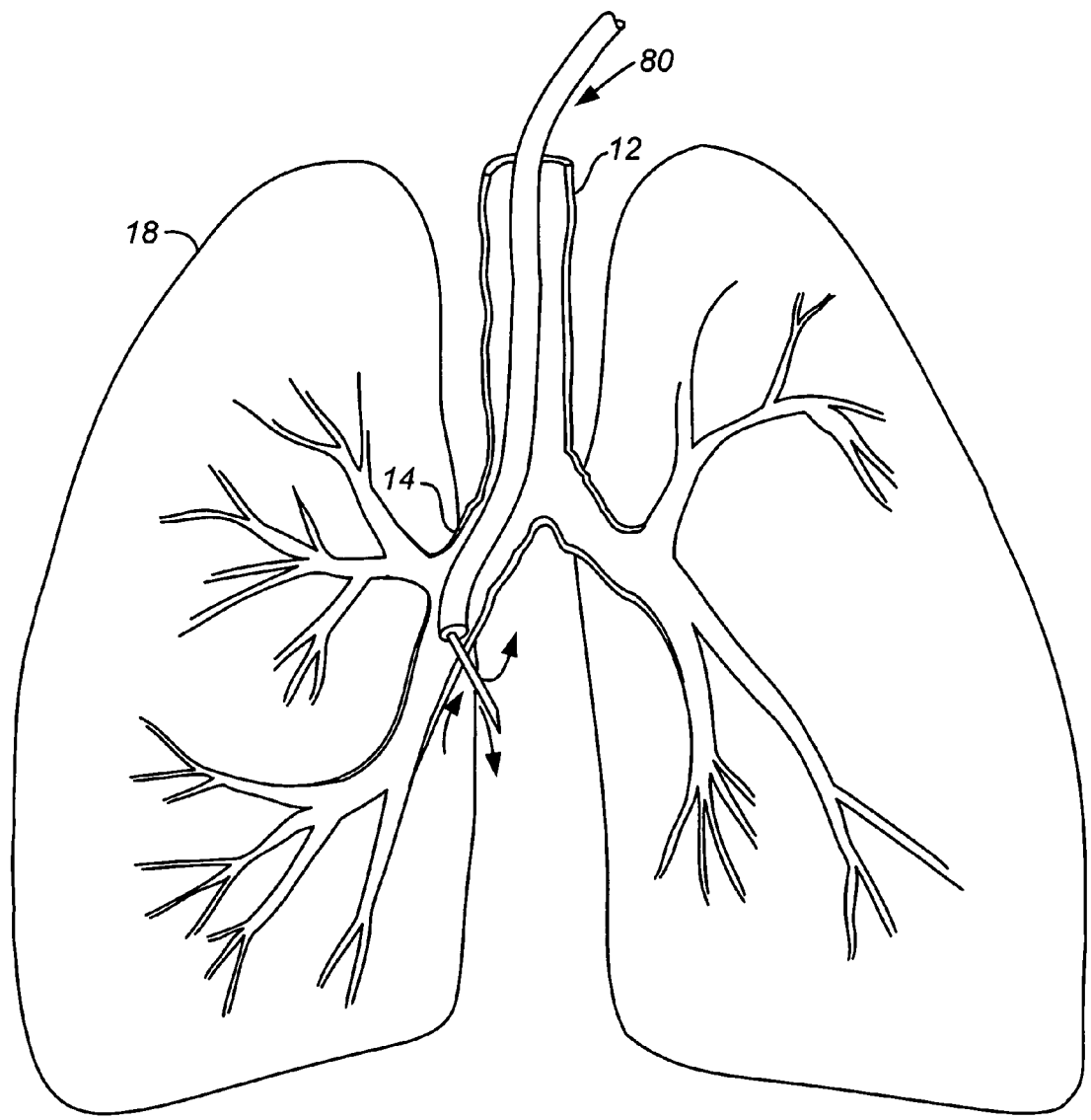

A variety of events can cause the pleural space to be violated and fill with gas (such as air) or fluid. For example, rupture of subpleural apical emphysematous blebs, smoking, and physical height resulting in great distending pressure on the alveoli over time can result in a spontaneous pneumothorax; while transthoracic needle aspiration procedures, subclavian and supraclavicular needle sticks, thoracentesis, mechanical ventilation, pleural biopsy, transbronchial lung biopsy, cardiopulmonary resuscitation and tracheostomy can result in iatrogenic pneumothorax. Pleural space can also be filled with fluid, such as blood, as a result of, for example, blunt trauma, penetrating trauma (including iatrogenic), non-traumatic or spontaneous neoplasia (primary or metastatic), blood dyscrasias, including complications of anticoagulation, pulmonary embolism with infarction, torn pleural adhesions in association with spontaneous pneumothorax, bullous emphysema, necrotizing infections, tuberculosis, pulmonary arteriovenous fistulae, hereditary hemorrhagic telangiectasia, nonpulmonary intrathoracic vascular pathology (e.g., thoracic aortic aneurysm, aneurysm of the internal mammary artery), intralobar and extralobar sequestration, abdominal pathology (e.g., pancreatic pseudocyst, splenic artery aneurysm, hemoperitoneum), and/or catamenial. For purposes of illustration of the effect a pneumothorax or hemothorax can have on the lung structure, FIGS. 2A-B depicts the lungs 19 during a procedure wherein a biopsy device 80 is deployed to obtain a tissue sample 82 and breaches the pleura. As a result of the breach, air inside the affected lung 18 exits the lung (indicated by arrows) around the opening 84 in the lining made by the device 80. As illustrated in FIG. 2B a device 86 is inserted into the trachea 12 and fed down the right primary bronchus 14 where the device 86 thereafter inadvertently punctures the wall of the bronchus 14. As in the previous example, air inside the affected lung 18 exits the lung (indicated by arrows) around the opening 88 created when the device 86 punctured the wall of the bronchus 14.

As will be appreciated by persons skilled in the art, the invention and its embodiments have been described for purposes of illustration with respect to diagnostic and treatment of lung tissue. However, certain aspects of the devices and methods, for example, the sealing component, are applicable to diagnostic and therapeutic procedures, including treatment modalities, and devices suitable for use elsewhere in a subject. Other areas of the body suitable for treatment or diagnostics include, but is not limited to, liver, connective tissue, pancreas, breast, kidney, gastrointestinal tract, brain, mediastinum, joints, bladder, and prostate. Treatment modalities include, but is not limited to, filling voids, repairing tissue lacerations, and repairing dissections.

Figure 3A:
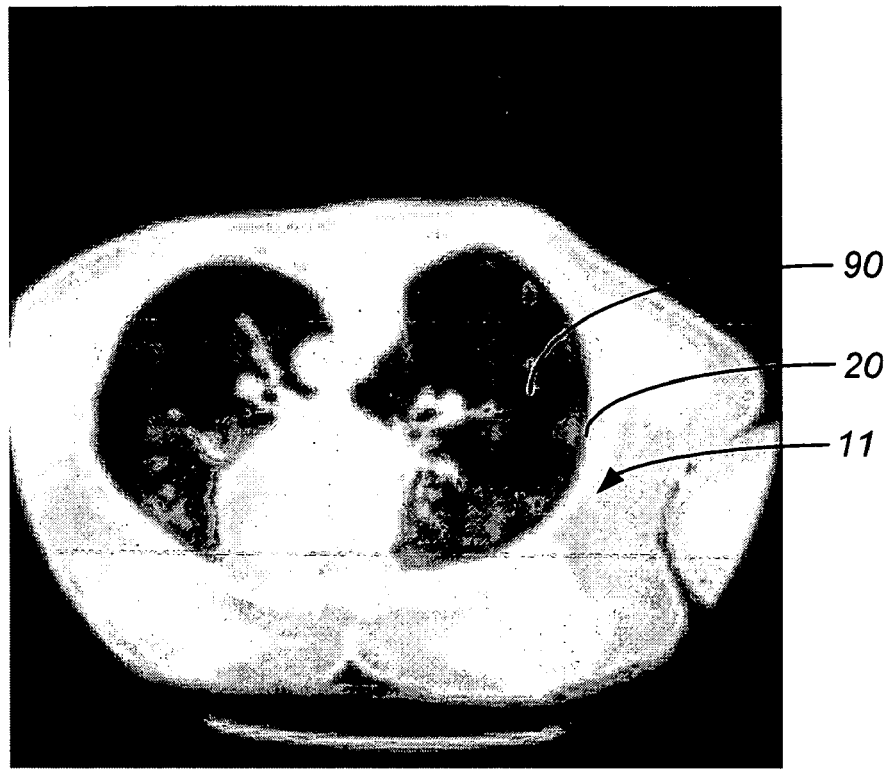
FIGS. 3A-B illustrate an image of a small pneumothorax which has progressed into a large pneumothorax during a transthoracic procedure.
Figure 3B:
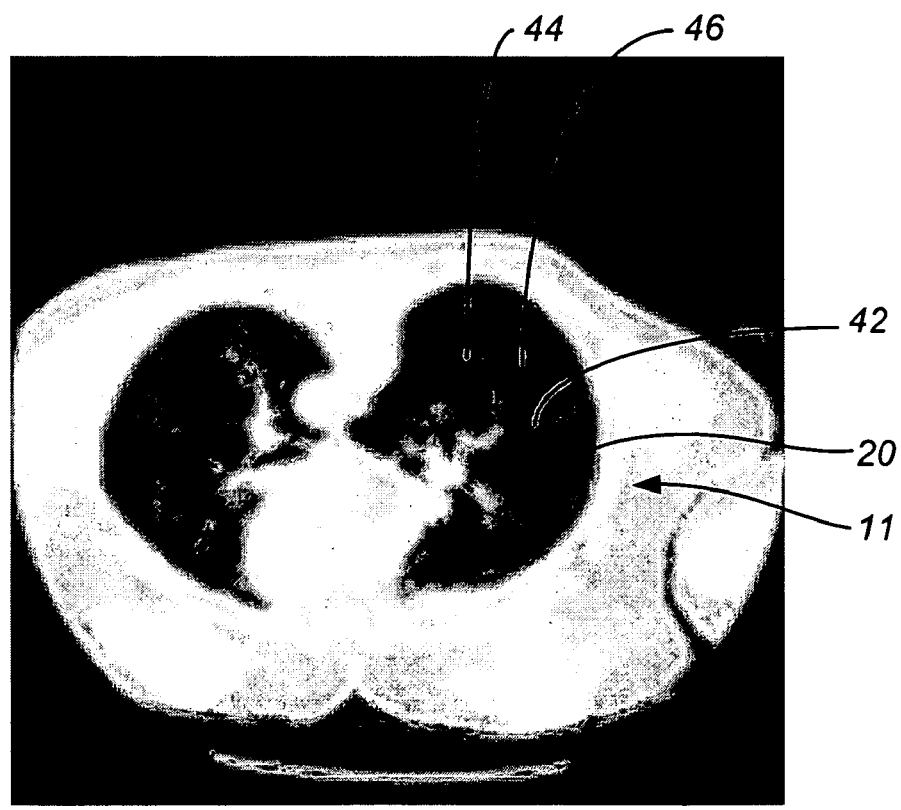

FIG. 3A illustrates an image of a cross-section of the thoracic cavity 11 taken during a fine needle aspiration procedure where a needle 90 has been inserted into the left lung 20 and breached the parietal pleura 44 and visceral pleura 42. Although care has been exercised during the procedure, a pneumothorax has resulted as illustrated in FIG. 3B. As shown, in a cross-section of the same thoracic cavity 11 taken shortly thereafter, the pneumothorax has progressed and the pleural space 46 has filled with air and the size of the left lung 20 has collapsed away from the parietal plurea 44.

Figure 4A:
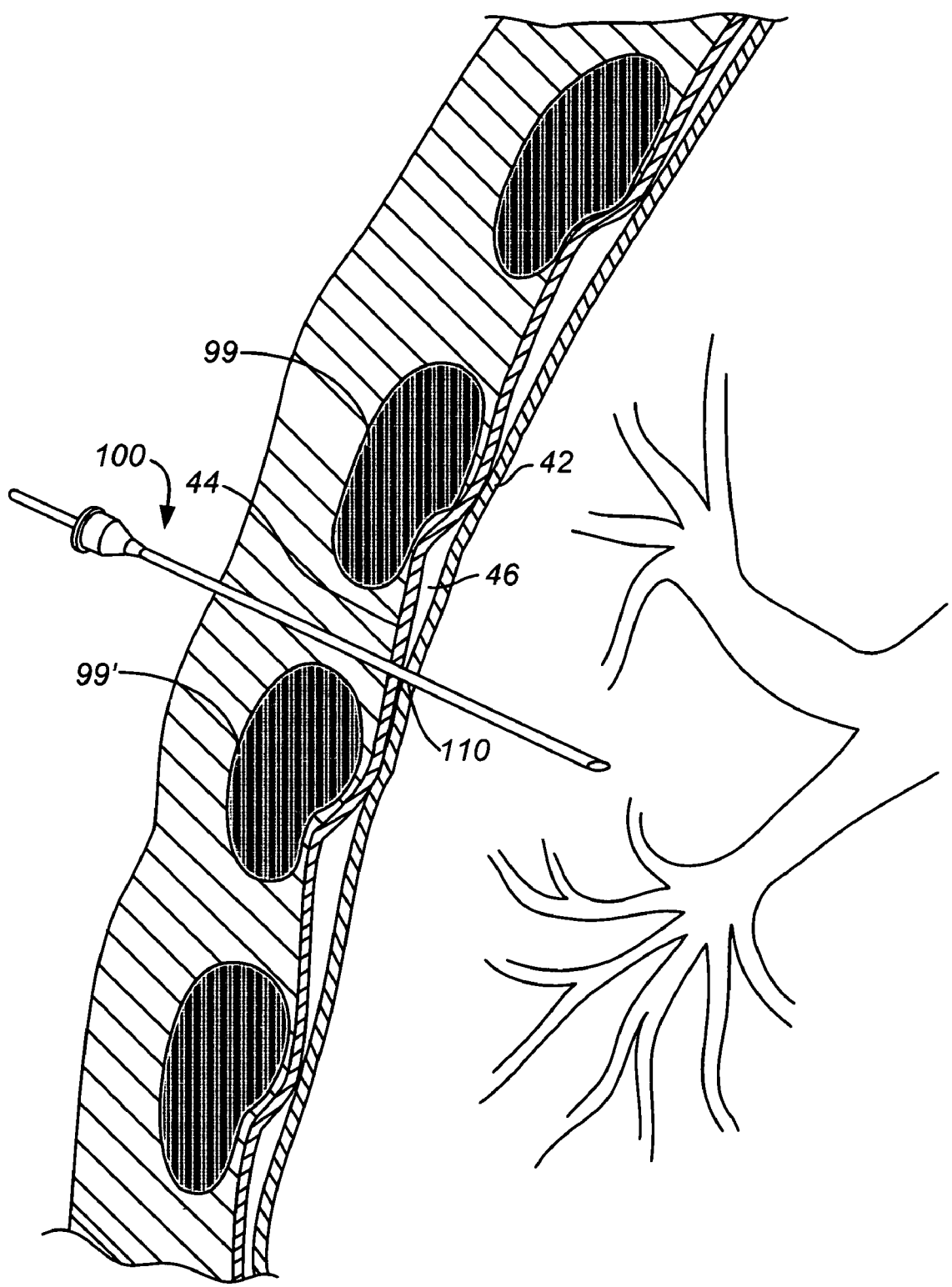
FIGS. 4A-B illustrate a device penetrating a pleura to access the interior of the lung; with the device sealing the entry tract as the device is removed.
Figure 4B:
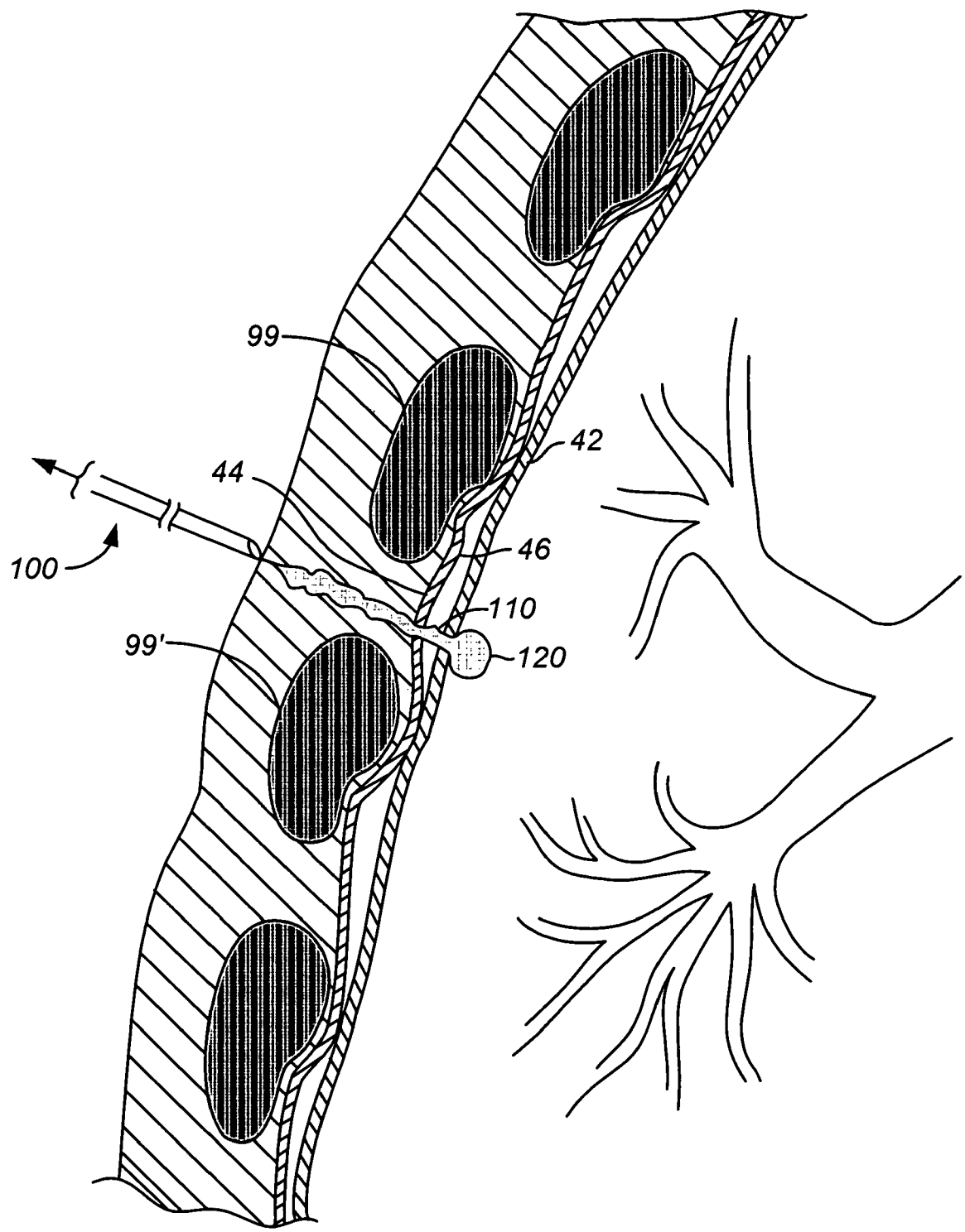

FIGS. 4A-B illustrate a device 100 configured according to an embodiment of the invention positioned between adjacent ribs 99, 99' in the rib cage before penetrating parietal pleura 44, the pleural space 46 and the visceral pleura 42 to access the interior of the lung. As illustrated in FIG. 4B, the device 100 is adapted to seal its entry path 110 with, for example, a biocompatible heat-treated glutaraldehyde glue 120 as the device 100 is removed. Sealing the entry path 110 provides several advantages, including preventing the pleural space 46 from being filled with gas (such as air) or fluid (such as blood) as a result of the procedure. Additionally, sealing the entry tract or wound 110 prevents migration of cells along the entry path 110 after the procedure. Thus, if a device 100 is inserted to obtain, for example, a tissue sample for biopsy and the tissue in or near the sample site has cancerous cells, sealing the entry tract prevents the migration of cells, including potentially dangerous cancer cells, into other areas.

Figure 5:
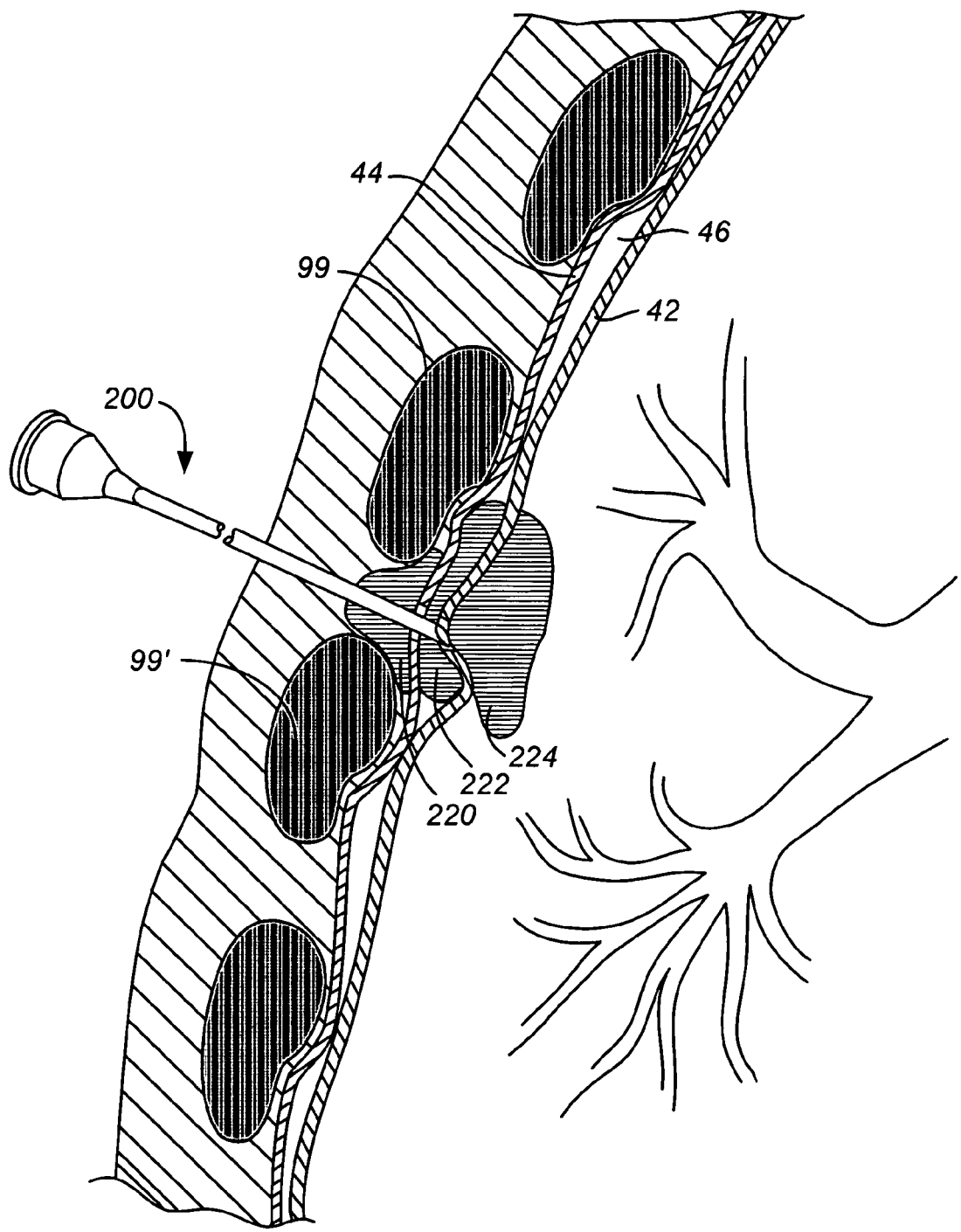
FIG. 5 illustrates a device used to pre-treat the access site at various locations for a target tissue location, such as pleura.

FIG. 5 illustrates a device 200 configured according to an embodiment of the invention adapted to pre-treat an intended entry path 110 with sealant 220, 222, 224 as described herein. For purposes of illustration, the device 200 has delivered a first sealant 220 on the proximal (exterior surface) of the parietal pleura 44, a second sealant 222 within the pleural space 46 and a third sealant 224 on the distal (interior surface) of the visceral pleura 42. As will be appreciated by those skilled in the art, a single one of the three sealants illustrated can be delivered without departing from the scope of the invention. Further, a combination of two of the three sealants illustrated can also be delivered without departing from the scope of the invention. Finally, as described above, this technique can be used with respect to other areas of the body and other treatment modalities without departing from the scope of the invention.

Figure 6:
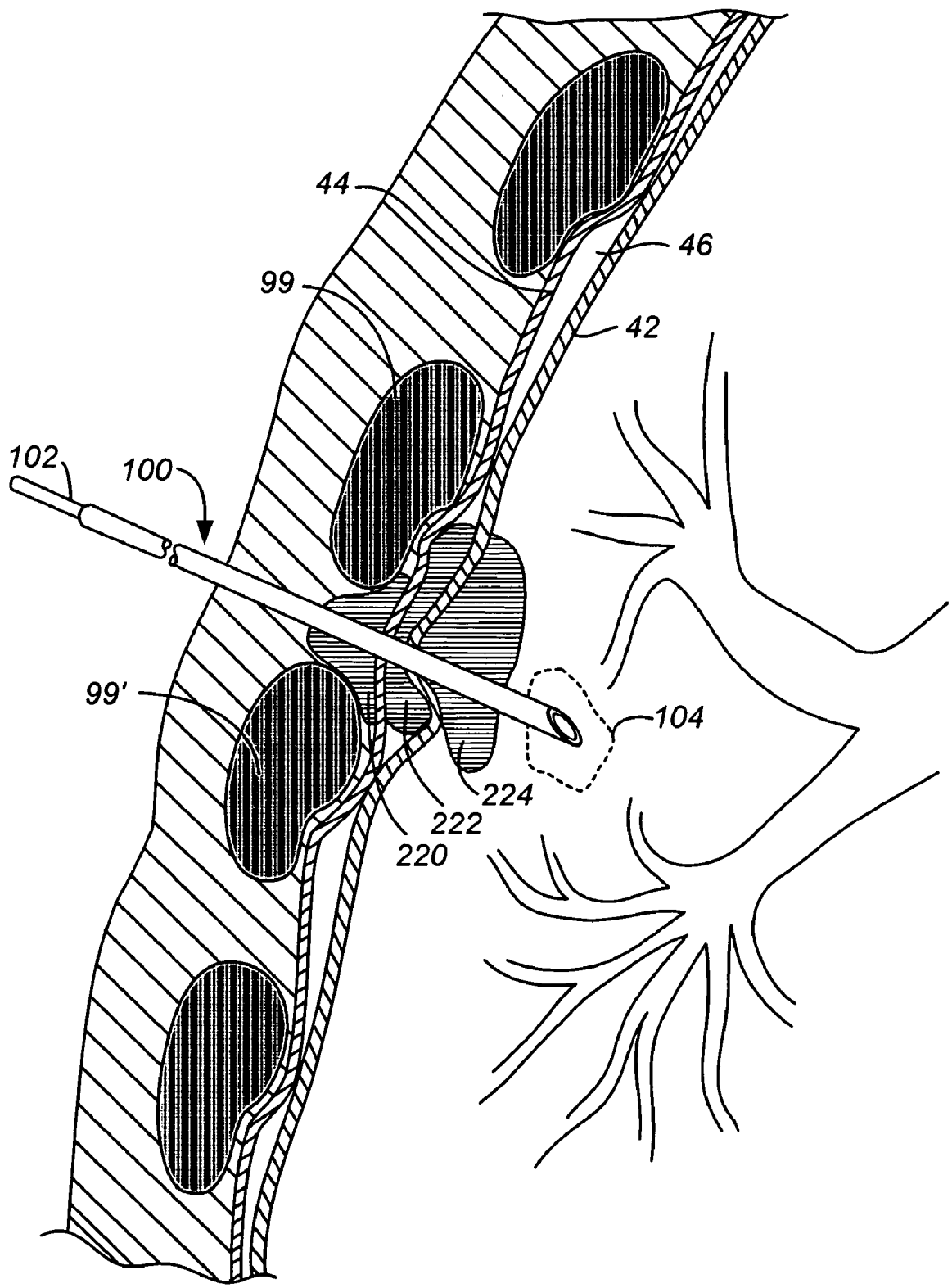
FIG. 6 illustrates a device having a wire stylet penetrating a pleura that has been pre-treated with sealant.

As illustrated in FIG. 6 a device 100 is inserted through the sealant 220, 222, 224 to enable a wire stylet 102 to access target tissue 104 within the lung space. Accessing the lesion through the pre-delivered sealant further prevents the procedure from resulting in a pneumothorax or hemothorax. Further, pre-delivering sealant to an access site can enable the use of large bore instruments as discussed below, previously not practical to employ, to access the lung. Where, as illustrated in FIG. 6, the device deployed is a smaller bore device the device can be inserted and removed through the pre-delivered sealant, without the additional step of delivering sealant through the entry tract upon withdrawal of the device. However, those skilled in the art will appreciate that the additional step of delivering sealant to the entry tract upon removal of the device can be practiced even for small bore devices. Further, where sealant is pre-delivered to an access site, the viscosity of the pre-treatment adhesive can be different than the viscosity of the adhesive used to close the entry path. Where adhesives of more than one viscosity are desired to be delivered during the process, the device can be adapted to provide multiple adhesive delivery mechanisms within the device.

Figure 7:
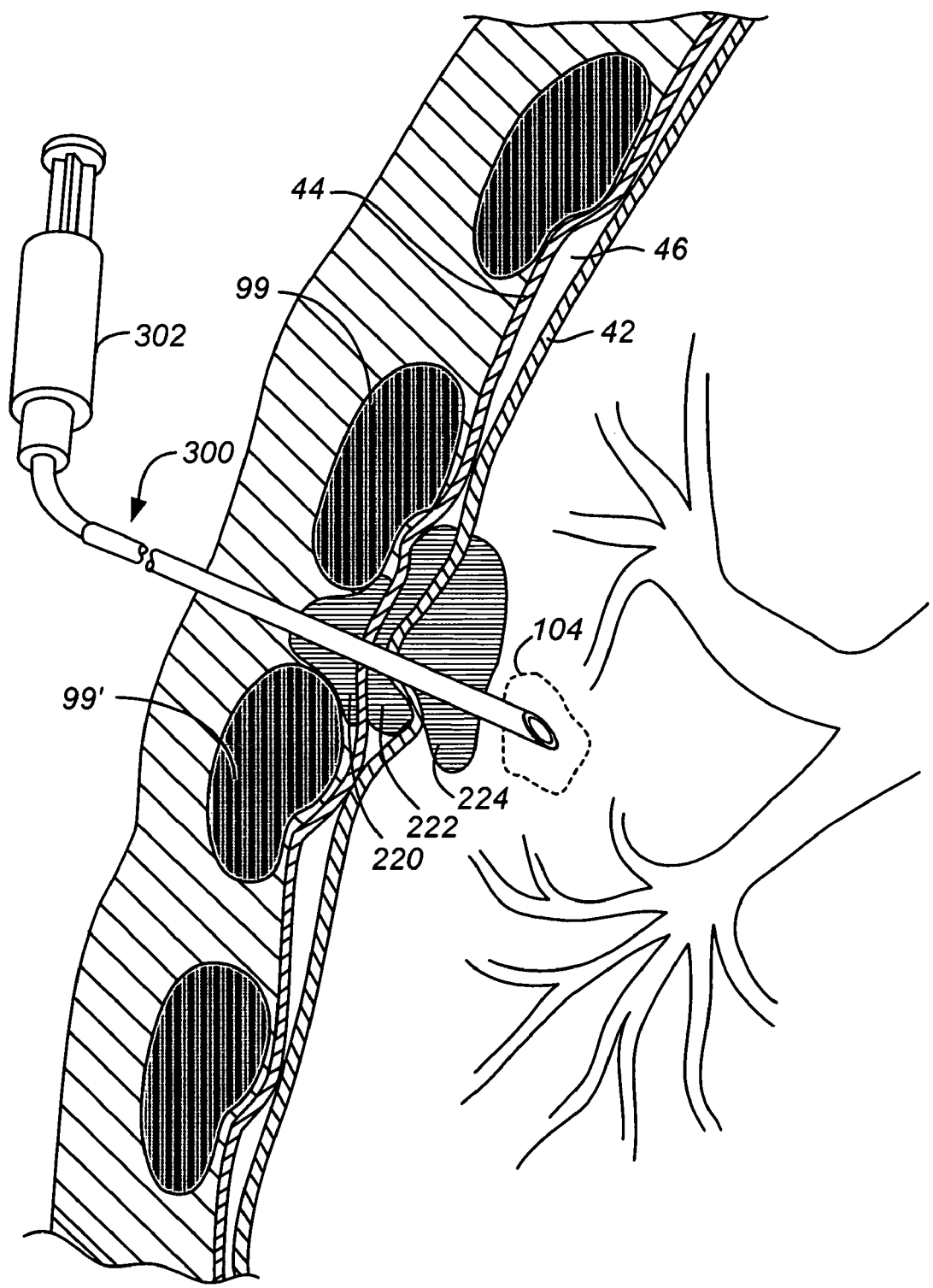
FIG. 7 illustrates a device adapted to communicate with a suction syringe penetrating a pleura that has been pre-treated with sealant to access lung tissue.

FIG. 7 illustrates a device 300 adapted to communicate with a suction syringe 302 penetrating adjacent ribs 99, 99' to penetrate a parietal pleurae 44, a pleural space 46, and a visceral pleurae 42 that has been pre-treated with sealant to access target tissue 104. In the illustrated embodiment, sealant 220, 222, 224 has been pre-delivered to the injection tract site to facilitate the use of a cannulated instrument having a larger bore to interface with the target tissue 104.

Figure 8A:
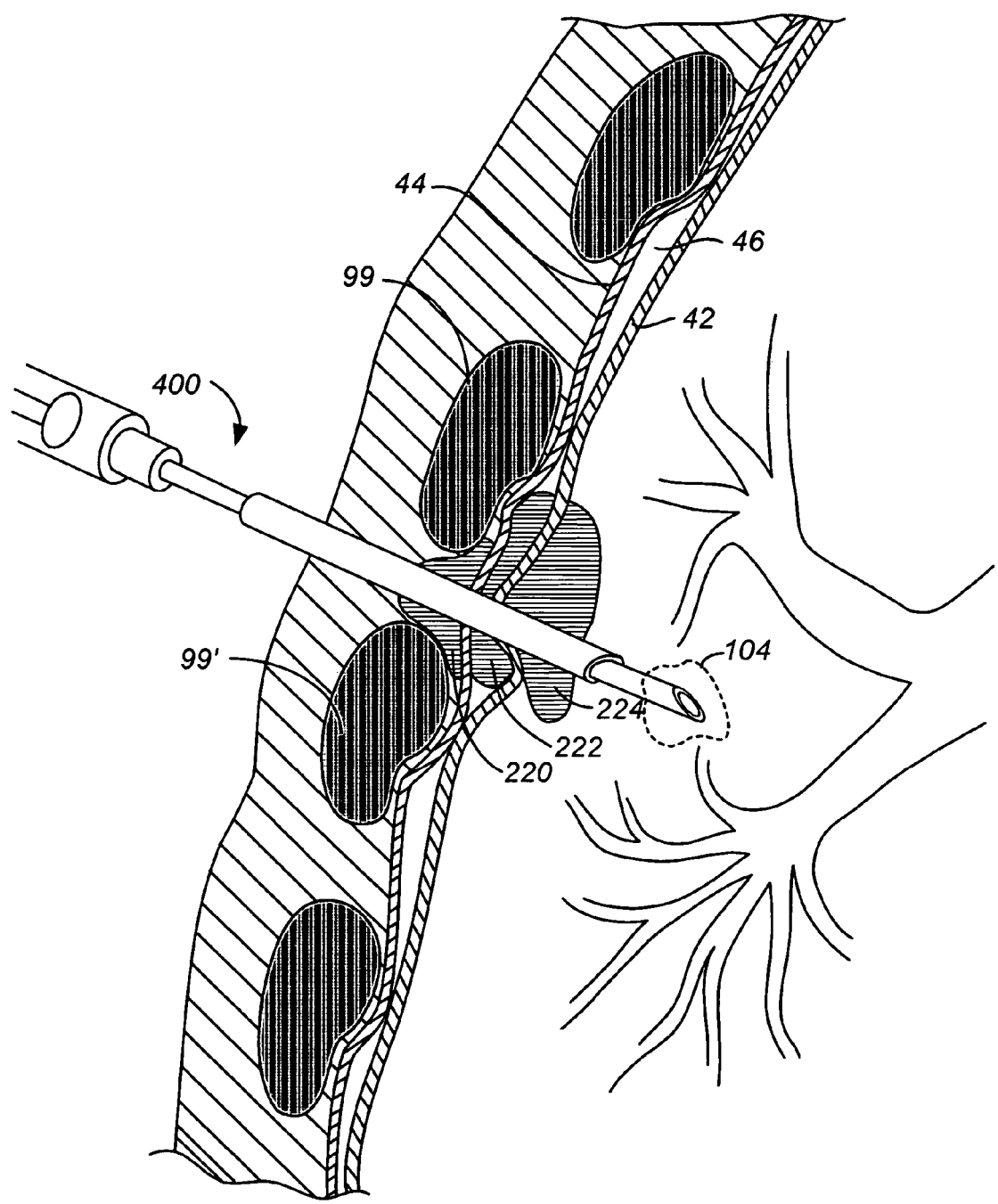
FIGS. 8A-B illustrate a therapeutic device removing lung tissue through a cannula that penetrates a pre-treated pleura.
Figure 8B:
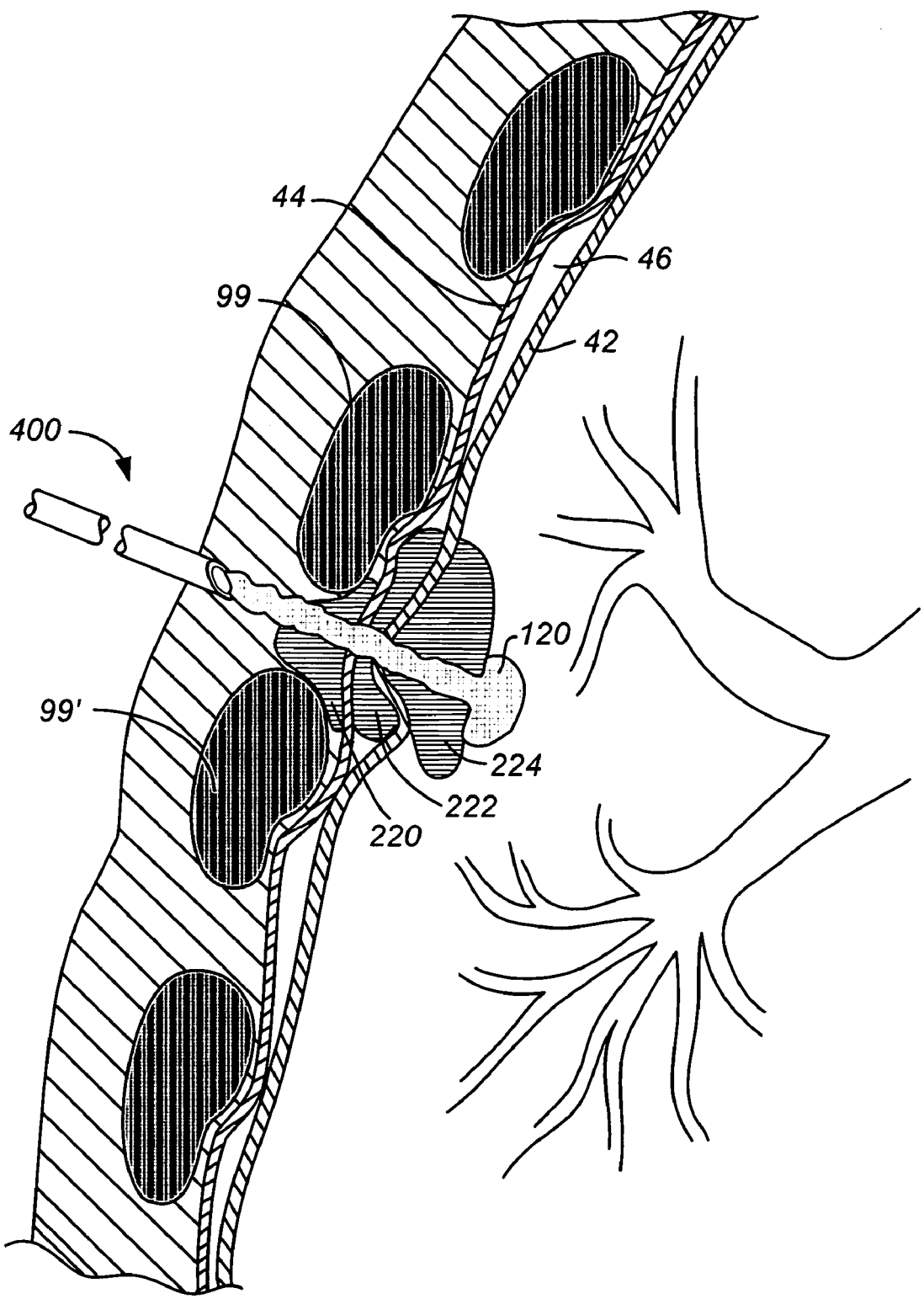

Turning to yet another embodiment, FIGS. 8A-B illustrate a therapeutic device 400 adapted to remove target tissue 104 through a cannula 108 that penetrates a pre-treated pleura having sealant 220, 222, 224. As discussed above, the use of a large bore device (such as a cutting device with a diameter of 0-1 inch or a gauge size of 1-22), can be more advantageously employed where the delivery tract 110 has been pre-treated with sealant and the device 400 is adapted to deliver sealant 120 into the delivery tract 110 during removal, as shown in FIG. 8B.

Figure 9A:
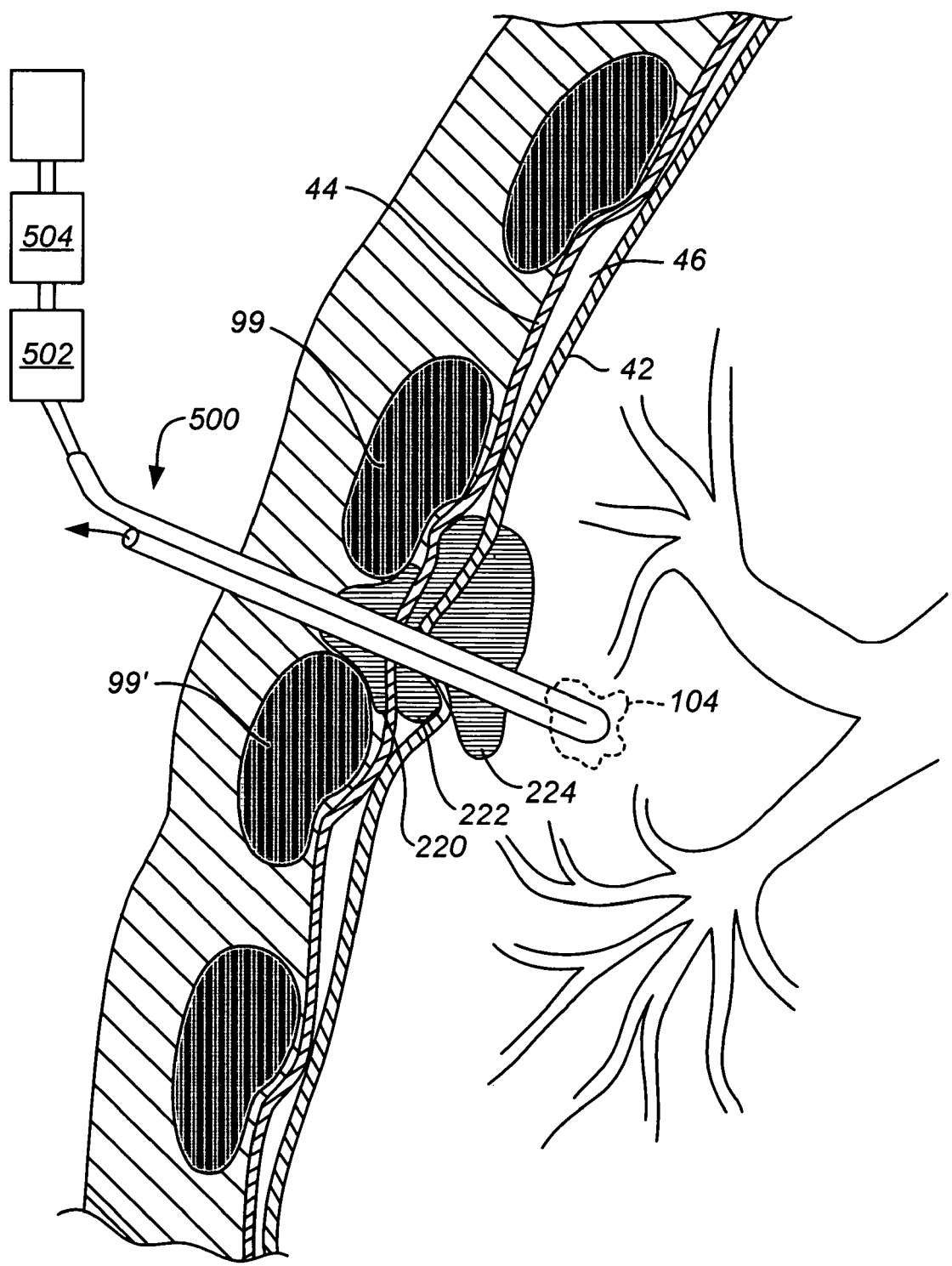
FIGS. 9A-B illustrate a device adapted to connected to a cryosurgical probe.
Figure 9B:
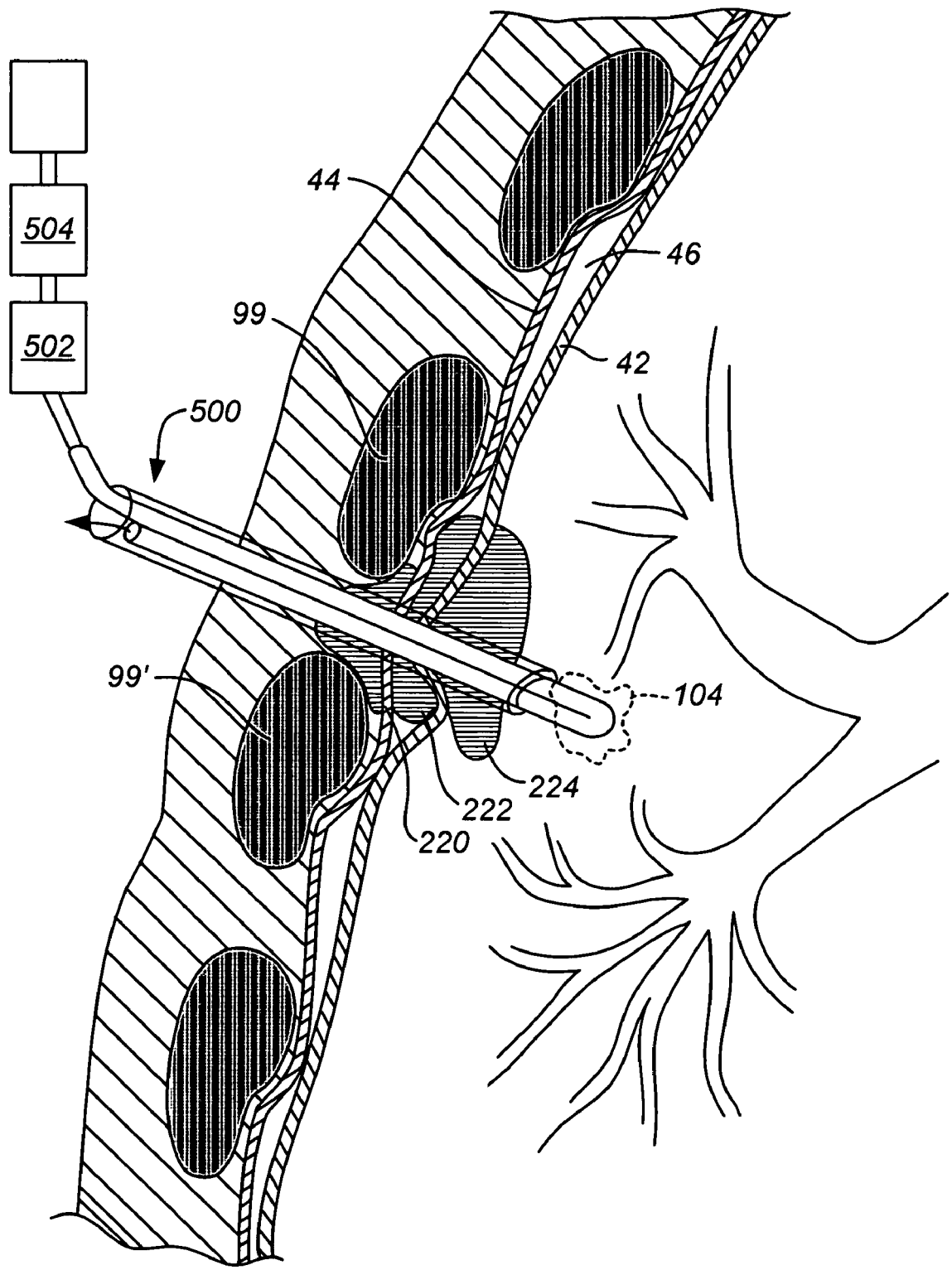

FIG. 9A illustrates another embodiment of the invention wherein device 500 is a cryosurgical probe. The cryosurgical probe 500 is connected to a switch 502 a regulator 504 and a $CO_2$ or liquid nitrogen source. Additional information about cryosurgical probes is available in U.S. Pat. No. 5,452,582. The cryosurgical probe is inserted penetrating between adjacent ribs 99, 99' to penetrate a parietal pleurae 44, a pleural space 46, and a visceral pleurae 42 that have been pretreated with sealant 220, 222, 224 to access target tissue 104. As persons skilled in the art know, the cryosurgical probe is suitable for performing cryosurgery, such as killing tissue in surgical procedures. FIG. 9B illustrates another embodiment of the invention wherein the device 500 has a sealant delivery device 501 adapted to deliver sealant into the delivery tract prior to or concurrent with removal of the device 500.

Figure 10:
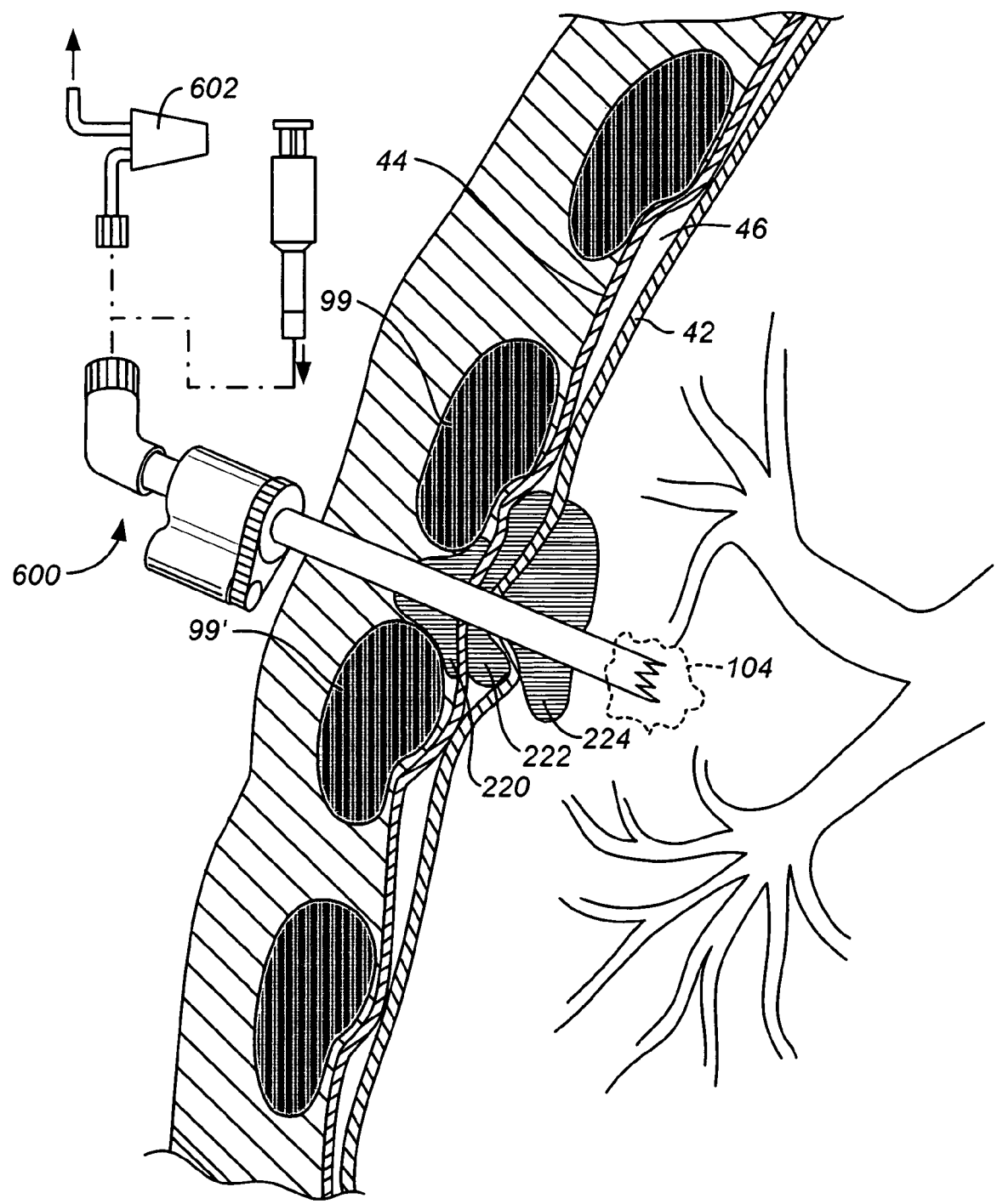
FIG. 10 illustrates a device adapted to connect to cutter for removal of tissue and a vacuum trap.

FIG. 10 illustrates a tumor excising device 600 adapted to connect to vacuum pump 602. The vacuum pump 602 is used to suction, for example to remove fluid.

Figure 11:
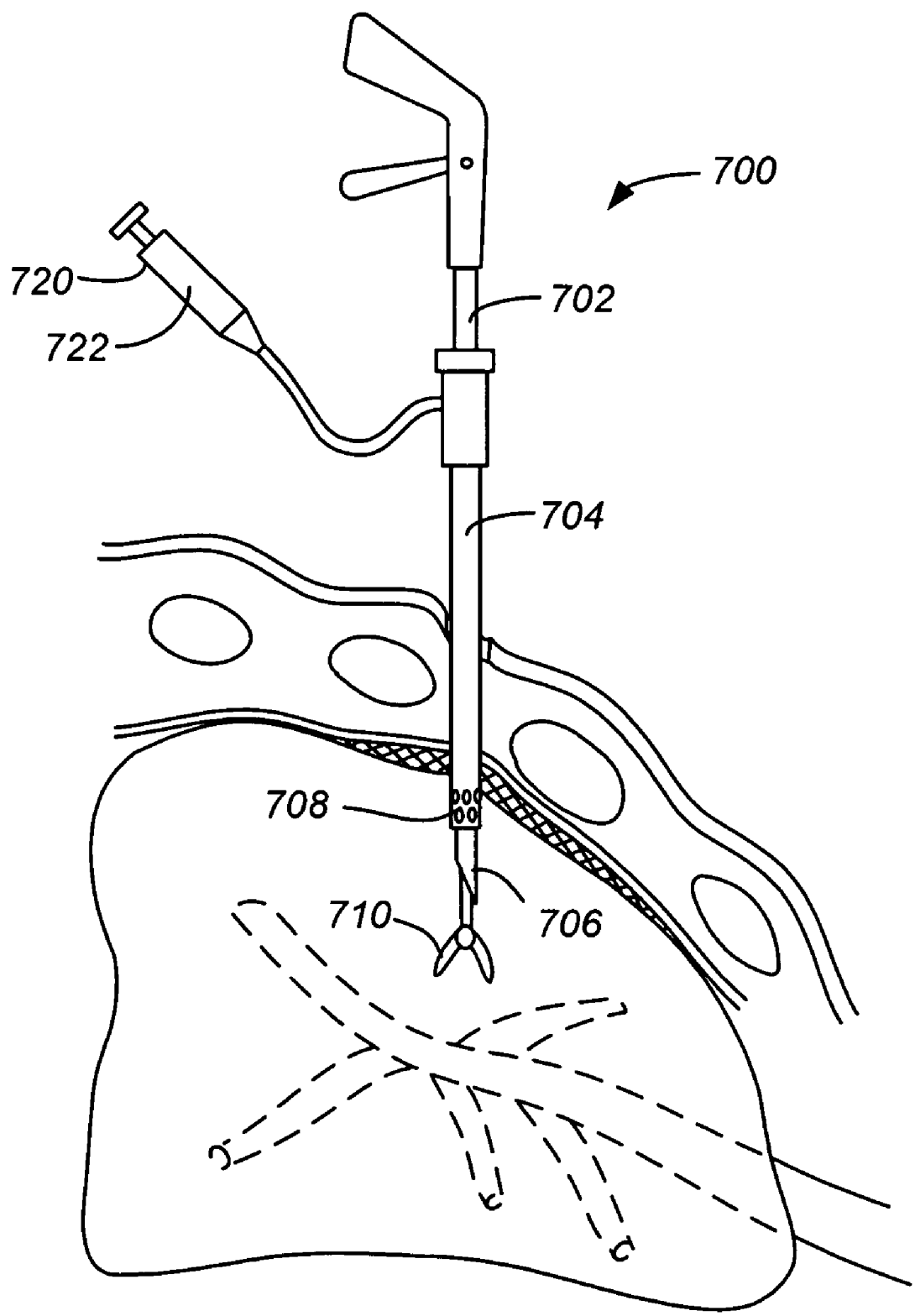
FIG. 11 illustrates a tool suitable for diagnostic and therapeutic uses with a sealant delivery element.

FIG. 11 illustrates a generic device 700 of the present invention. Device 700 has a tool 710 at the distal end of an elongated body 702 adapted to make contact with, and perform some function on, an inner part of the lung or the surrounding tissue through an access hole or other hole. Lung device 700 also has a hole closing element 720 for closing the access hole. As shown in FIG. 11, body 702 is disposed within a sleeve 704 or other dilating device, with tool 710 extending from the distal end of the sleeve. Tool 710 and body 702 may be inserted through sleeve 704 after the sleeve is in place within the body. Alternatively, tool 710 and body 702 may be partially or completely disposed within sleeve 704 during insertion of sleeve 704 into the patient through an access hole. Sleeve 704 may also have a sharp distal end 706 to form the access hole.

In one embodiment, hole closing element 720 is adapted to deliver biologically compatible sealant to close the access hole. A syringe 722 may be operated by the user to deliver sealant to the area of the hole or incision through perforations 708 at the distal end of sleeve 704. Preferably, the tool is withdrawn from the sleeve 704 before delivering sealant to the site. Alternatively, the sealant may be delivered through sleeve 704 around the tool body 703.

Although many alternative sealant formulations may be suitable for this purpose, a preferred sealant would consist of primarily a combination of stable polyaldehyde, albumin, including porcine albumin and collagen with or without additional additives. The sealant can also have agents that initial or accelerate the clotting cascade so the sealant can be used as a hemostatic agent. For example, a suitable material is described in US Patent Application Publ. No. 2004/0081676. This sealant works as a biologic glue that cures within a few minutes to seal pleural layers without causing inflammation or heat. The glue's intrinsic viscosity can be tuned to allow for fast or slow delivery through a delivery system, such as those shown above and includes glue viscosity more than 1.1 centipoise. This glue formulation is appropriate for use with all lung tissue and structures within the pulmonary system as well as pulmonary vasculature. It can also be formulated and used for any adhesive or anti-adhesion purpose including anastomosis of blood vessels and bronchi/bronchioles and to seal pulmonary structures from air leaks, bleeding or fluid leaks. Ideally, the sealant will cure within a few minutes, works well in a damp or wet environment, and blocks air or fluid from entering the pleural cavity. Typically, the glues are composed of a condensation product of glutaraldehyde that consists of cross-linked albumin, including porcine albumin. Adhesion values for the glue can be up to 1.5 psi, more preferably between 0.2-0.6 psi.

Alternative sealant formulations may be suitable to achieve these goals such as a combination of any one of the previously described components in combination with other additives that may include elastin, fibrin, glycoprotein, liposomes, thrombin, calcium, neuroleptics, vitamins, growth factors, glucocorticosteroids, steroids, antibiotics, antibacterial compounds, bacteriocidal and bacteriostatic compounds, antiviral compounds, antifungal compounds, antiparasitic compounds, tumoricidal compounds, tumoristatic compounds, toxins, enzymes, enzyme inhibitors, proteins, peptides, minerals, neurotransmitters, lipoproteins, glycoproteins, immunomodulators, immunoglobulins and fragments thereof, dyes, radiolabels, radiopaque compounds, fluorescent compounds, fatty acids, polysaccharides, cell receptor binding molecules, anti-inflammatories, antiglaucomic compounds, mydriatic compounds, anesthetics, nucleic acids and polynucleotides.

The sealant may be delivered to the incision site as a sealant delivery device according to the embodiments herein, is withdrawn from the incision to seal, for example, the pleural lining, blood vessels, airways, or other holes, apertures, or channels formed during the procedure. Alternatively, sealant may be delivered before the device is withdrawn from the incision. The sealant and its delivery system may be bundled together with one or more tools in a kit to perform particular therapeutic or diagnostic procedures.

In the embodiment shown in FIG. 11, tool 710 is a grasper. In other embodiments, the tool may be a cutting element (e.g. having a diameter of 0-1 inch or a gauge size of 1-22), a needle, forceps, a scalpel, a scraper, brushes, scissors and other ablation tools, such as RF loops, heaters, laser ablation, probes, mechanical excision devices, x-ray, radiation, cryosurgical probes and other devices. The sealing function enables a wide range of different sizes of these cutting elements to be used for purpose of the present invention. In particular, the biopsy devices of the present invention can include large-size cutting elements that would otherwise be unsuitable for lung biopsy because of their propensity to cause pneumothorax or hemothorax. Details of designs for the tool portion of the device would be apparent to those skilled in the art. Details of suitable tool designs can be found in U.S. Pat. Nos. 6,902,536; 5,599,294; 5,916,210; 6,080, 113; 6,267,732; 6,540,694; 6,638,275; 6,689,072; 6,716,180; 6,730,044; 6,808,525; 6,825,091; 6,840,948; 6,902,526; 6,902,536.

Many of these agents cause tissue binding to form localized adhesions or a bio-response that will help maintain permanent bonding. Introduction of these materials instigates one or more elements of a tissue remodeling cascade process. The process includes tissue polymer decomposition and/or necrosis that leads to recruitment of cellular respondents that include one or more of the following: Neutrophils, white blood cells, macrophages, CD8+, MMP's, Interlukens, cytokins and protocylins. The tissue then remodels to initiate tissue formation and thickening that culminates in the formation of tissue adhesions.

Other materials that can initiate this effect are cadmium, smoke artifacts, tars, materials that irritate tissue such as alcohols, solvents, organic solvents, acids, materials that are basic and materials that are acidic. These materials include compounds or compositions that have pH levels between 1 and 6.9 with materials closest to 1 being a preferable acid material. Additionally, compounds or materials that have pH levels between 7.5 and 14 work very well; materials closest to 14 work best.

Figure 12A:
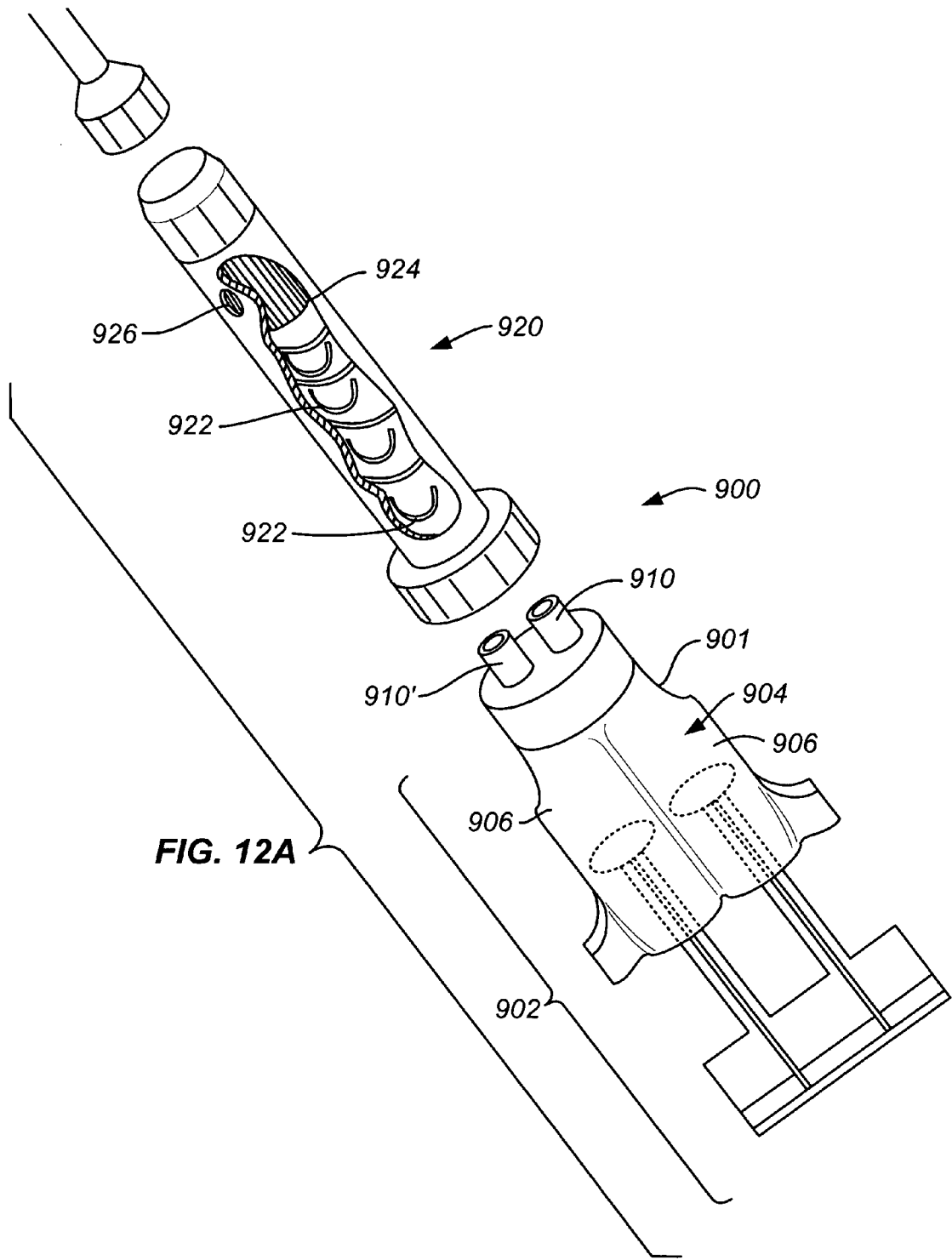
FIGS. 12A-B illustrate a delivery device with a dual chamber for holding sealant components prior to delivery, and a delivery cannula.
Figure 12B:
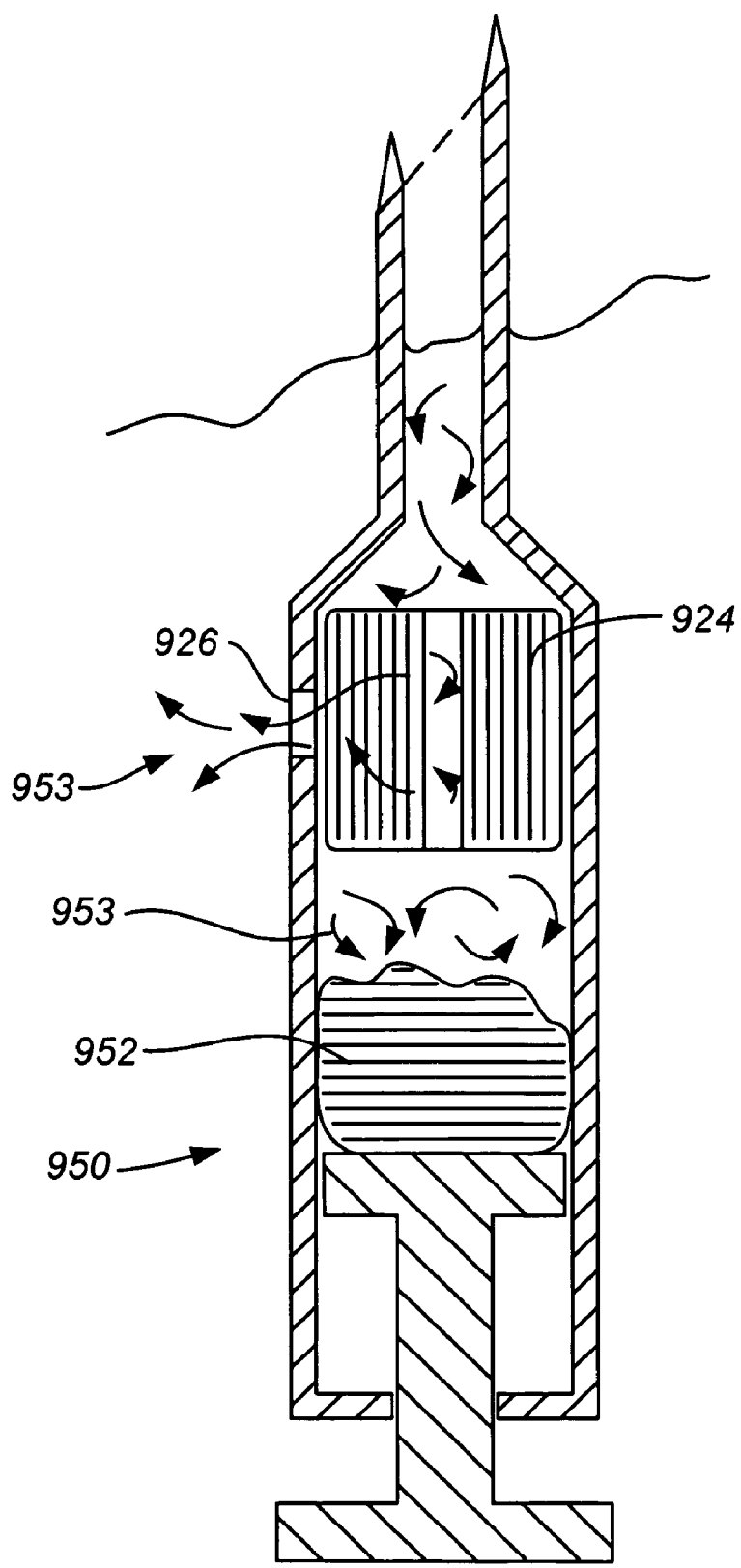

Some adhesives can be formed as, for example, two-part compositions. FIG. 12A illustrates the sealant delivery portion of the device 900. The proximal end 902 of the device 900 features the dual chamber 904 delivery housing 901. The sealant delivery housing is separated into at least two chambers 906, 906' in order to separate components of the sealant to be delivered. The two parts of a two-part adhesive composition can be delivered down the separate channels of the device 900. A plunger 908 is provided to advance the glue components down each chamber of the delivery housing. The glue components are advanced through separate sealed tips 910, 910 in order to facilitate easily replacing the stir chamber 920 in the event of a clog. The sealant delivery housing 901 is easily separable from the stir chamber 920 to facilitate replacement during a procedure. The stir chamber 920 receives the glue components from the at least two ports of the sealant delivery housing. Mixing elements or baffles 922 are provided within to mix the glue components together as the components advance down the stir chamber 920. The mixing chamber can have prongs that interact with tips to break its seals when the mixing chamber is connected to the device. The distal end of the stir chamber 920 features a porous plug filter 924 that enables air to escape the stir chamber 920 through an air bleed hole 926 located on the side of the stir chamber 920 at its distal end. Suitable filters include microfilters available from GenProbe. The filter properties are such that air can be dispersed through the filter transverse to the axis of the glue while the glue will be forced axially through the filter. FIG. 12B illustrates another delivery device having a plunger 950 advancing glue 952 through a chamber while air 953 is advanced through a porous plug filter 924 where it can exit through the air bleed hole 926 before the glue is delivered through the cannula into the target tissue.

Embodiments of the device may also include an imaging element to aid in the diagnosis and/or treatment of a condition. The imaging element may be connected to the distal end of the elongated body. The type of imaging element to be coupled to the elongated body will vary depending on the intended application in which the subject device is to be employed. In general, to view a subject's lung or any specific parts thereof, the imaging element may comprise a camera, preferably a microcamera, even more preferably a digital microcamera equipped to transmit real-time images of the lung tissues. Additionally, the imagining element may include visualization light fiber bundles, laser light fibers, light canes, and light tubes. Moreover, the imaging element may include an ultrasonic probe, or preferably, a magnetic resonance imaging (MRI) probe to provide high-resolution images of different layers of the lung and the surrounding tissues. A particularly suitable MRI probe is described in U.S. Pat. No. 6,549,800.

The subject device can also be coupled to a delivery element adapted to channel a pharmaceutical composition to the lung. The element is typically connected to the proximal end of the elongated body. The element can be any access structure familiar to skilled artisans, which can store and release the pharmaceutical composition upon reaching a desired site of the lung or the surrounding areas. Non-limiting exemplary delivery elements include tubes and catheters which are known in the art. For example U.S. Pat. No. 4,739,760.

In an alternative embodiment, the hole closing element may deliver a plug, a clip or sutures to close the hole. For example, the hole closing element may deliver expanding plugs that use a polymer covered NiTi frame. Solid collagen, ceramic or polymer plugs can be placed so that the plug can clip the lung wall to the chest wall. Expanding stents made from NiTi, Ti, stainless steel or polymer can be placed to anchor the lung and seal the pleura from air leaking in. The stent devices can be covered with silicone, polyurethanes, polyethelynes, nylons, Dacron, ePTFE, PTFE, Chronoprene, Chronoflex or other biocompatible polymers or other folded or elastic material that help prevent air leakage. Clip designs may be placed to secure the pleura walls and then a plug can be placed inside the clip to seal off potential air leakage into the pleural space. The hole may also be sutured closed using minimally invasive suturing tools either delivered through sleeve 704 or inserted into the incision after sleeve 704 and/or tool 710 has been withdrawn.

A variety of materials are suitable for fabricating the patient-contacting elements of the present invention. In general, the materials are inert so that they do not readily react with the biologically compatible sealant under physiological buffer conditions and/or body temperatures. Non-limiting examples of such materials include glass, semi-conductors such as silicon and germanium, metals such as platinum and gold, and a vast number of plastic polymers. Exemplary plastic polymers include polyamide (PA), polyimide (PI), polyacrylonitrile (PAN), polybutylene (PB), polybutadiene (PBD), polycaprolactam (PCL), polyethylene (PE), polychlorotrifluoroethylene (PCTFE), polytetrafluoroethylene (PTFE), polydimethylsiloxane (PDMS), polyethylene terephathalate (PET), polyisobutylene (PIB), polystyrene (PS), polyolefine (PO), polymeric polyisocyanate (PPI), polyvinylchloride (PVC), polyvinylidene chloride (PVDC), polyvinyl fluoride (PVF), acrylonitrile-acryloid-styrene (AAS), acrylonitrile-butadiene-styrene (ABS), acrylonitrile-chlorizate ethylene-styrene (ACS), and any other inert polymers provided by commercial vendors.

The devices of the present invention provide effective tools for a variety of diagnostic and/or therapeutic interventions. Accordingly, in one embodiment, the invention provides a method of performing a lung biopsy in a subject. The method comprises the steps of delivering a biopsy device to a site within the subject's lung or surrounding tissue of the lung, where a biopsy sample is to be taken; obtaining a biopsy sample from the lung; and using the biopsy device to apply a biologically compatible sealant to the lung.

Figure 13:
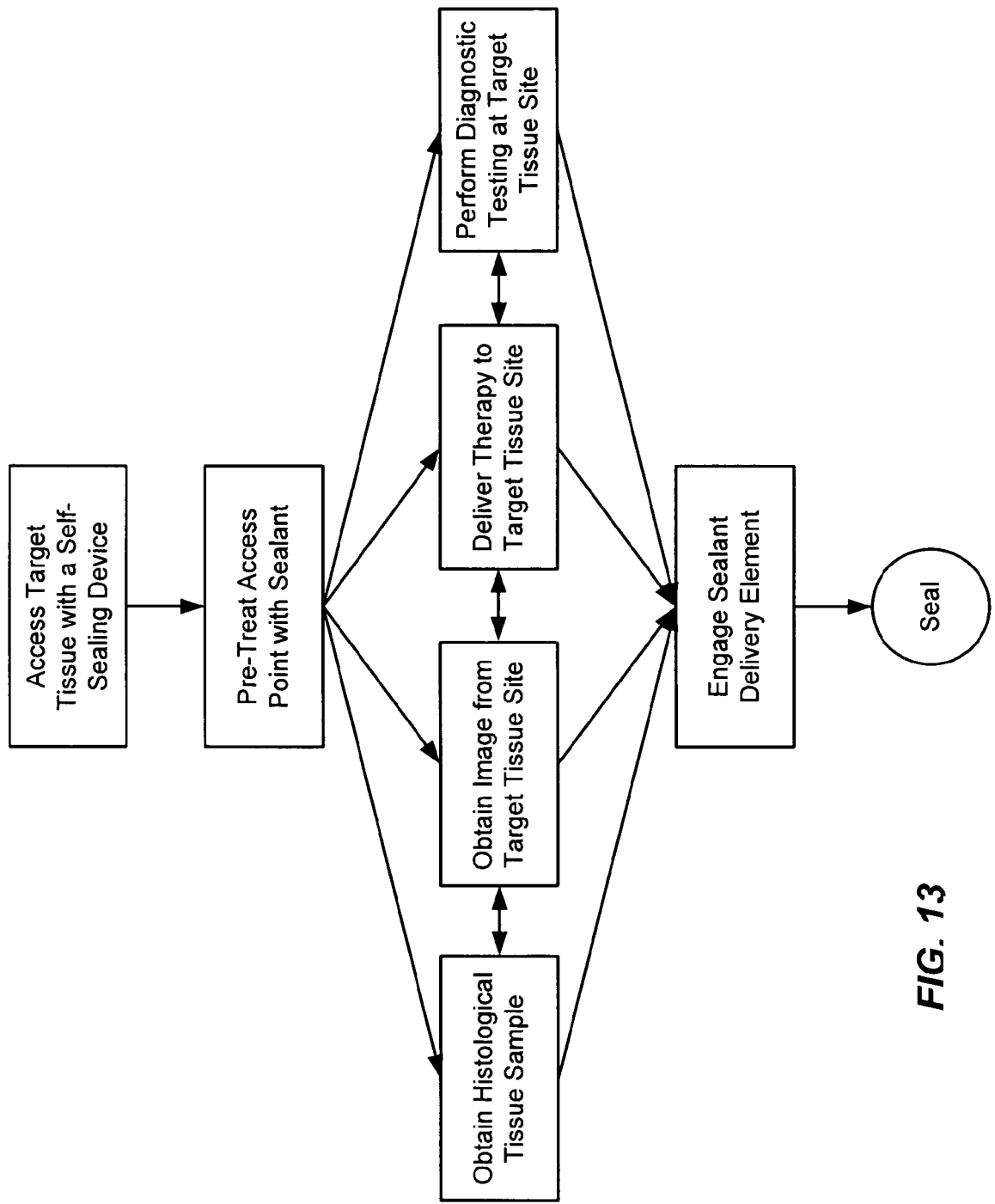
FIG. 13 is a flow chart illustrating the steps of a method practiced under the invention.

As described above, the devices are adapted to mitigate air and fluid leakage into a space between the pleural membrane. The devices are particularly suited for mitigating pneumothorax or hemothorax while accessing tissue from the thoracic cavity. As illustrated in FIG. 13, the procedure can involve (a) accessing a thoracic cavity and then, e.g., (b) obtaining a biopsy sample from any part of the lung or the surrounding tissue, (c) imaging a portion or the entire lung, (d) delivering a pharmaceutical composition, (e) excising tissue, or (f) any combination of the above. After the desired therapeutic or diagnostic procedure, or combination thereof, has been performed, the device is removed while sealing the access tract of the device to prevent migration of tissue or cells into the tract and to prevent fluid or air from entering the cavity. Optionally, the sealant can also be pre-applied to the access hole.

In another embodiment, the present invention provides a method of preventing, for example, pneumothorax or hemothorax, resulting from accessing a subject's lung or surrounding tissue of the lung with the use of the external device. Such method comprises delivering the external device to gain access to the subject's lung or the surrounding tissue; and using the device to apply a biologically compatible sealant to the lung. Depending on the intended application, the subject methods can be used to view, biopsy, and treat one or more lobes of the lung, namely, the right upper lobe, the right middle lobe, right lower lobe, the left upper lobe, and the left lower lobe. Sealant can be delivered before the therapeutic or diagnostic procedure, during the procedure, or following the procedure (e.g. as the device is removed).

Sealant components for this application may include fibrin/thrombin, activated PEG/PEG-diamine, albumin/PEG, and albumin/glutaraldehyde sealants. The sealant is an implantable material that may contain hemostatic agents such as chitin derivatives including but not limited to carboxymethyl chitin and chitosan (1-100% deacetylated). The sealant components may also contain additives that affect viscosity, set time, adhesion, and biocompatibility. The albumin component may be formulated in weight to weight ratios of 10-50% where the remaining mass balance is aqueous solutions of salts, buffers, and additives or combinations thereof. The other component of the sealant is a cross-linker containing glutaraldehyde, heat treated glutaraldehyde, processed glutaraldehyde (PGA), or derivatives thereof in weight to volume ratios of 1-25% where the remaining balance is an aqueous solution with or without additives, salts, or buffers or combinations thereof. These solutions may be applied from dispensers that deliver a ratio of 1 unit volume of protein solution per 1 unit volume of cross-linker solution (1:1 protein:cross-linker) and may be applied in ratios up to 10 unit volumes of protein solution per unit volume of cross-linker solution. Furthermore, mixing may occur by passing the solutions through a static mixing tip with helical or other geometrical devices that enhance the mixing efficiency. Sealants prepared from these solutions contain 5-45% protein and 0.5-14% crosslinker.

Other suitable sealants and other agents are described in US Pat. Appl. Publ. No. 2004/0052850; US Pat. Appl. Publ. No. 2004/0081676; U.S. Ser. No. 11/008,577; U.S. Ser. No. 11/008,092; U.S. Ser. No. 11/008,094; U.S. Ser. No. 11/008,578; U.S. Ser. No. 11/008,649; U.S. Ser. No. 11/008,777; U.S. Ser. No. 11/008,087; U.S. Ser. No. 11/008,093; U.S. Ser. No. 11/008,580; and U.S. Ser. No. 11/008,782.

Materials that solidify such as glue compositions form a structure that is typically stiffer than the intrinsic stiffness of lung tissue. Specifically, pull tests of lung parenchyma (comprised of alveolar sacks and collagen) sections show that the composite stiffness is very low. When agents are combined that form a stiffer structure than the underlying biomaterial or lung tissue, the modulus mismatch causes irritation, inflammation, tissue thickening, fibrosis, a remodeling cascade and adhesions that will promote and maintain lung volume reduction. Compositions that dry out or maintain viscosity levels above 2 centipoise (a measure of dynamic viscosity) generate shear and cause this stiffness mismatch to promote adhesions. Agents and hydrogel materials thicker than 10 centipoise work better. The glutaraldehyde glue technology employed can produce compositions that have 15 centipoise viscosity and higher levels up to and beyond 150 centipoise. By increasing the glue cross-linking properties, agents can be delivered that solidify to a gel or harder substance. Materials that gel to produce solids with a modulus greater than 10-20 centimeters of $H_2O$ will produce this same effect. Materials that are stiffer in a range between 20 and 100 centimeter of $H_2O$ are better. Materials that are stiffer than 100 cm $H_2O$ are preferable. Implantable materials with viscosity enhancing agents to promote these effects can be manufactured.

Many of these agents cause tissue binding to form localized adhesions or a bio-response that will help maintain permanent pleurae bonding. Introduction of these materials instigates one or more elements of a tissue remodeling cascade process. The process includes tissue polymer decomposition and/or necrosis that leads to recruitment of cellular respondents that include one or more of the following: Neutrophils, white blood cells, macrophages, CD8+, MMP's, Interlukens, cytokins and protocylins. The tissue then remodels to initiate tissue formation and thickening that culminates in the formation of tissue adhesions.

Other materials that can initiate this effect are cadmium, smoke artifacts, tars, materials that irritate tissue such as alcohols, solvents, organic solvents, acids, materials that are basic and materials that are acidic. These materials include compounds or compositions that have pH levels between 1 and 6.9 with materials closest to 1 being a preferable acid material. Additionally, compounds or materials that have pH levels between 7.5 and 14 work very well; materials closest to 14 work best.

When applying an implantable hydrogel comprised of a biocompatible material, or an implantable liquid that undergoes a physical transition from a liquid to a gel or other solid such as solid adhesives, control of deposition is very important. Ways of controlling deposition include localized dispensing of the sealant through a suitable device containing a lumen, and also through the addition of agents that increase the viscosity of one or more components of the implantable material. Such agents include biocompatible materials with viscosities that are greater than those of water, and include glycerol, polymeric materials such as proteins, carbohydrate-based polymers and derivatives thereof, synthetic materials including polyethylene glycols (PEG), polyethylene oxides (PEO), polyvinyl pyrrolidone (PVP), polyvinyl alcohol and other components described in the "United States Pharmacopeia" and the "Handbook of Pharmaceutical Excipients", edited by A. H. Kibbe. Other materials for controlling viscosity include oils, lipids, and fatty acids, including oleic acid, and phosphocholines. Phase separation can be controlled with emulsifiers including poly sorbate. For sealants prepared by mixing two or more components, the viscosities of one or more of the components can be modified by adding an appropriate agent to control spreading after application. Viscosities of these components can range from 1 to 1000 centistokes (a measure of kinematic viscosity).

Deposition and control of spreading of sealants containing two or more components are also affected by the gel time, or set time, of the mixed sealant. Sealants with short set times are preferably to those with longer set times. Ideal set times for the present invention and method range from 1-600 seconds, and preferable from 1-60 seconds. Set time can be controlled by the addition of set time modifiers, including agents that reduce or increase the set time relative to the corresponding formulation lacking the set time modifier. An example of an agent that decreases the set time is carboxymethyl cellulose. An example of an agent that increases the set time is glycerol.

Glutaraldehyde, as currently processed and used in some commercial sealants, undergoes reversible reactions that cause reoccurring inflammation. These properties can be improved by chemical modification of the glutaraldehyde. One such modification includes glutaraldehyde condensation reactions, as described in "Bioconjugate Techniques" by G. T. Hermanson. This condensation involves the formation of derivatives of glutaraldehyde in aqueous solutions containing acid or base. This reaction can be monitored by ultraviolet spectroscopy at or near 280 and 234 nanometers. At 280 nanometers, pure glutaraldehyde has significant absorbance, and little or no absorbance at 234 nanometers when measured as an aqueous solution at 0.5% weight to volume. When glutaraldehyde is chemically modified, it has significant absorbance at 234 nanometers. These derivatives are effective cross-linking agents when used with nucleophilic substrates such as proteins, including albumins. Furthermore, sealants prepared from glutaraldehyde derivatives are adhesive in vivo, through chemical or mechanical means, or a combination of chemical and mechanical means.

Implantable materials for the present invention are any agents administered into tissue, including sealants, which may be comprised of hydrogels, proteins, or other biocompatible materials, that can be implanted into compromised tissue to benefit the patient. Examples of hydrogels include those prepared from natural sources including carbohydrate-based materials. Such materials include hyaluronans, hyaluronic acid, alginates, chitins, chitosans, and derivatives thereof. Proteins that enable the present invention include albumins, including porcine albumins, collagens, gelatins, and other proteins that can be cross-linked or that form solutions with viscosities greater than water. Although a wide variety of collagenous tissue can be employed, low collagen content collagenous tissue, such as lung parenchyma and pleura, are particularly suitable. Other implantable materials include those prepared by mixing two or more components so that a viscous solution, gel, or solid is formed. Such implantable materials are prepared from a protein substrate where the protein is derived from natural, synthetic, or semi-synthetic processes. The protein may also be derived from recombinant DNA technology and may be isolated from cell-culture processes, as well as from transgenic plants and animals. Examples of proteins include albumins, including porcine albumins, collagens, and gelatins. Cross-linkers employed as part of the implantable material precursors include aldehydes, polyaldehydes, esters, and other chemical functionality suitable for cross-linking protein(s). Examples of homobifunctional cross-linking agents are described in "Bioconjugate Techniques" by G. T. Hermanson.

Materials of the invention, e.g., the cross-linked protein adhesives and heat-treated glutaraldehyde glues, when subjected to a swell test, have values in a percentile range lower than 100. To determine the swell test value, the material is placed in water and allowed to hydrate. The hydrated material is then weighed. Following the step of weighing the hydrated material, the hydrated material is then dried (e.g. by heating) and weighed again to determine a dry weight. The ratio of these two weights (hydrated vs. dry) comprises the result of the swell test and indicates how much moisture a material can take on in a percentage of its weight. Thus, for example, most non-glutaraldehyde glues typically have a swell test of 100-150%, which makes the glue come apart in a moist environment. Fibrin based glues have an even higher swell test value. Cross-linked albumin based glues of this invention have a lower swell test value which enables the glues to perform well in moist environments, with a swell test value ranging from −50% to 100%.

The implant components, including the cross-linking agent and the substrate, can be formulated at a pH in the range of 5-10 by adjusting the pH and/or by adding suitable buffers in the range of 1-500 mM. Examples of buffers include phosphate, carbonate, bicarbonate, borate, or imidazole, or mixtures thereof. Additionally, additives or stabilizers may be added to improve the stability of one or more of the components. Furthermore, imaging agents may be added to allow for detection of the material. Such agents include iodine, iodine compounds, metals such as gadolinium, radioisotopes, and other compounds for gamma scintigraphy, magnetic resonance imaging, fluoroscopy, CT, SPECT and other imaging modalities. Additionally, the material may be formulated such that the mechanical properties are suitable for applications in the specific tissue to which the implantable material is applied. Such properties include elasticity, modulus, stiffness, brittleness, strain, cohesion, adhesion, and stress. Agents for modifying the properties include fillers, plasticizers, and adhesion modifiers. Furthermore, the implant may induce a natural adhesive mechanism with or without the addition of chemical agents which may be added to the implant to induce a natural response. Such agents include particles in the range of 100 nm to 1 millimeter. Agents include chemical or biochemical agents (proteins or nucleic acids) that induce a natural response. Examples of such agents include bleomycin, cytokines and chemokines, and single stranded RNA molecules.

In some embodiments, it may be desirable to use bioabsorbable sealants that expand or swell in the presence of aqueous fluids such as biological fluids. A commonly used sealant of this type includes both natural and synthetic hydrogels. Synthetic hydrogels can be prepared from the following classes of polymers and these are generally considered to be non-biodegradable: poly(hydroxyalkyl methylacrylates) such as poly(glyceryl methacrylate)poly(acrylamide) and poly(methacrylamide) and derivativespoly(N-vinyl-2-pyrrolidone)anionic and cationic hydrogelspoly(vinyl alcohol) poly(ethylene glycol) diacrylate and derivatives from block copolymers composed of poly(ethylene oxide)-poly(propylene oxide)-poly(ethylene oxide) and poly(propylene oxide)-poly(ethylene oxide)-poly(propylene oxide) blocks, respectively. All of these materials can be cross-linked with agents such as ethylene glycol dimethacrylate or methylene-bisacrylamide. Biodegradable synthetic hydrogels can be prepared from polymers such as those listed above by incorporating one or more of the following monomers: Glycolide, Lactide, e-Caprolactone, p-Dioxanone and Trimethylene CarbonateIn addition. Exemplary hydrogels based on natural products include polypeptides such as gelatin and polysaccharide such as starch and dextran. These natural products can be further processed by cross-linking with formaldehyde, glutaraldehyde and various other dialdehydes.

The biologically compatible sealant of the present invention may also comprise a detectable label. The detectable labels suitable for use in the present invention include any composition detectable by spectroscopic, photochemical, biochemical, immunochemical, electrical, optical or chemical means. A wide variety of appropriate detectable labels are known in the art, which include luminescent labels, radioactive isotope labels, and enzymatic labels. In preferred embodiments, one will likely desire to employ a fluorescent dye or label. These exemplary labels may be incorporated by a number of means well known to those of skill in the art. For instance, the label can be mixed with the sealant. Alternatively, labels can be chemically conjugated to the sealant molecules.

The use of a detectable label is particularly desirable for imaging the pleural region. The specific imaging means will depend on the particular type of label being used. For instance, radioactive labels can be detected by X-ray imaging. Fluorescent labels can be detected by an array of fluoroscopic equipment commonly employed by artisans in the field.

Ideally the composition of the sealant enables it to perform in a wet tissue environment. As is known in the art and discussed above, fibrin glue alone does not operate well in a wet environment and has been abandoned for use in many medical applications because of its inability to perform in a wet environment. The sealants used herein, in combination with the devices and methods, provide high adhesion in a wet environment. The adhesion of the sealant is beyond a low threshold that fibrin provides in wet tissue.

In determining an appropriate sealant to use with the devices and methods, two pieces of thin collagen based tissue (e.g. 1 inch wide by 2 inches long) are submerged into water ($H_2O$) or saline. The glue or sealant to be tested is then applied to the surface of one of the pieces and the two pieces are placed together in the water bath. The testing environment and materials are maintained at 67-69° F. The glue or sealant joint between the two layers of collagen is formed within 2 minutes of removing the tissue from the fluid without benefit of drying. The test section is 1 square inch of overlapped tissue that is glued with the excess tissue extending out both ends so that the two pieces can be gripped independently. The ends are gripped and pulled in opposite directions to test the force to shear the 1 inch section apart. The result is measured as shear stress or shear pressure and is recorded as pounds force per unit area. Currently available fibrin glues tested using this method fail at approximately 0.0-0.2 pounds force per square inch. Sealants and glues with a composition suitable for this invention fail at levels above 0.2 to well above 3.0 depending on the formulation.

In determining an appropriate sealant to use in another embodiment, the sealant is tested for biocompatibility based on MEM Elusion tests and the Agar Overlay tests.

In the MEM Elusion test, solids with uniform surface area and thickness of around<0.5 mm: 120 $cm^2$, solids with uniform surface area and thickness>0.5 mm: 60 $cm^2$, solids without uniform surface area of 4 grams, or liquids up to 10 mL are tested. The samples are extracted in a serum-supplemented mammalian cell culture media (MEM). Extractions may be performed in 0.9% saline or cell culture media without serum if desired. Samples are then extracted for 24-25 hours at 37±1° C. in 5±1% $CO_2$. The extracts are then filtered and placed in contact with a monolayer of L-929 cells (mouse fibroblasts). The cells are incubated at 37±2° C. in 5±1% CO2 for 48±3 hours, 72±3 hours or whatever incubation time is desired. The cells are then scored for cytopathic effect. The L929 cell line is the most commonly used for the test, however, as will be appreciated by those skilled in the art, other cell lines may be suitable as well.

Agar Overlay tests typically are used for solids of 300 $mm^2$ or 300 mg and liquids of 3 mL. In the Agar Overlay test, a layer of agarose mixed with cell culture media is placed on top of a monolayer of L929 cells (mouse fibroblasts). The samples are placed on top of the agar layer. The cells are incubated for a minimum of 24 hours at 37±1° C. in 5±1% $CO_2$. The cells are scored for cytopathic effect. The L929 cell line is most commonly used for testing. However, as will be appreciated by those skilled in the art, other cell lines can be used without departing from the scope of the invention.

Using either the MEM Elusion test or the Agar Overlay test result, the sealant should have a cytotoxicity, on a scale from 0-4, of 0 or 1, even if the sealant has glutaraldehyde to improve adhesion in the composition.

In practicing the subject methods, one may choose to remove the device while concurrently applying the biologically compatible sealant to the lung. Alternatively, the biologically compatible sealant may be applied shortly after the removal of the device, so long as the lapse of time does not cause a substantial risk of pneumothorax.

As noted above, the device of the present invention can be used for therapeutic intervention. Accordingly, in some embodiments, the subject methods are practiced to deliver a pharmaceutical composition alone, or in conjunction with diagnostic interventions including but not limited to imaging and biopsy. Where desired, the selected pharmaceutical composition can be delivered to one or more lobes in the lung, namely, the right upper lobe, the right middle lobe, right lower lobe, the left upper lobe, and/or the left lower lobe.

In the preferred embodiments, the pharmacological composition comprises a therapeutically effective amount of the active ingredient to provide the desired effect. Non-limiting examples of pharmacological composition are anti-inflammatory drugs, chemotherapeutic drugs, immunosuppressive agents, antihistaminics, analgesics, tranquilizers, antianxiety drugs, narcotic antagonists, antimigraine agents, coronary, cerebral or peripheral vasodilators, hormonal agents, antithrombotic agents, diuretics, antihypertensive agents, cardiovascular drugs, opioids, and the like. Preferred pharmaceutical compositions are therapeutics for treatment of pulmonary diseases, including but not limited to chronic obstructive pulmonary disease and lung cancer.

The amount of pharmacologically active ingredient administered and the dosing regimen used will, of course, be dependent on the particular drug selected, the age and general condition, or the pharmacological condition of the subject being treated, the severity of the subject's condition, and the judgment of the prescribing physician.

The above descriptions with reference to certain illustrated embodiments and certain exemplary practices are provided as a guide to a practitioner of ordinary skill in the art, and are not meant to be limiting in any way.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of performing tissue treatment or diagnosis in a subject, comprising:

inserting a device into the subject and toward a lung along an entry path;

pre-applying a cross-linkable tissue sealant from a sealant delivery element of the device to a region disposed along an external surface of a parietal parenchyma, within a plural space, and/or along an interior surface of a visceral pleura of the lung of the subject;

advancing the device, after pre-applying the sealant, along the entry path and through the pre-applied sealant to a target site within the lung of the subject; and performing treatment or diagnosis at the site.

2. The method of claim 1, further comprising removing the device while concurrently applying a biologically compatible tissue sealant to the lung.

3. The method of claim 1, wherein the sealant delivery element is adapted to mitigate air leakage into a space between the lung and pleural membrane.

4. The method of claim 1, wherein the sealant delivery element is adapted to mitigate pneumothorax.

5. The method of claim 1, wherein the sealant delivery element is adapted to mitigate hemothorax.

6. The method of claim 1, wherein the device further comprises an imaging element.

7. The method of claim 1, wherein the device further comprises a delivery element adapted to deliver a pharmaceutical composition to the lung.

8. The method of claim 1, wherein the device comprises a distal end comprising a cutting element for excising tissue, the method comprising removing tissue from the lung with the device so as to perform a lung biopsy.

9. The method of claim 1, wherein the sealant delivery element is a syringe.

10. The method of claim 1, wherein the sealant delivery element is a plunger.

11. The method of claim 1, wherein the biologically compatible tissue sealant is tissue-bonding material.

12. The method of claim 1, wherein the sealant comprises material selected from the group consisting of hydrogels, proteins, polymers and cross-linking agents.

13. The method of claim 12, wherein the hydrogel material comprises material selected from the group consisting of hyalurons, hyalyronic acid, alginates, chitins, chitosans, and derivatives thereof.

14. The method of claim 12, wherein the protein material comprises material selected from the group consisting of albumins, porcine albumins, collagens and gelatins.

15. The method of claim 12, wherein the polymer material comprises material selected from the group consisting of poly(lactic acid) and poly(glycolide).

16. The method of claim 12, wherein the cross-linking agent material comprises material selected from the group consisting of glutaraldehyde and stable polyaldehyde.

\* \* \* \* \*